United States Patent
Chodorowski-Kimmes

(10) Patent No.: US 10,993,902 B2
(45) Date of Patent: May 4, 2021

(54) HAIR DYEING PROCESS USING A PIGMENT, A MALEIC ANHYDRIDE ACRYLIC POLYMER AND AN AMINE COMPOUND

(71) Applicant: L'OREAL, Paris (FR)

(72) Inventor: Sandrine Chodorowski-Kimmes, Aulnay-Sous-Bois (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 16/500,738

(22) PCT Filed: Apr. 9, 2018

(86) PCT No.: PCT/EP2018/059049
§ 371 (c)(1),
(2) Date: Oct. 3, 2019

(87) PCT Pub. No.: WO2018/185345
PCT Pub. Date: Oct. 11, 2018

(65) Prior Publication Data
US 2020/0101004 A1    Apr. 2, 2020

(30) Foreign Application Priority Data
Apr. 7, 2017 (FR) .................................... 1753075

(51) Int. Cl.
| | | |
|---|---|---|
| *A61Q 5/10* | (2006.01) | |
| *A61K 8/81* | (2006.01) | |
| *A61K 8/41* | (2006.01) | |
| *A61K 8/898* | (2006.01) | |
| *A61K 8/92* | (2006.01) | |
| *A61Q 5/06* | (2006.01) | |

(52) U.S. Cl.
CPC .............. *A61K 8/8164* (2013.01); *A61K 8/41* (2013.01); *A61K 8/817* (2013.01); *A61K 8/8152* (2013.01); *A61K 8/898* (2013.01); *A61K 8/92* (2013.01); *A61Q 5/065* (2013.01); *A61K 2800/43* (2013.01); *A61K 2800/882* (2013.01); *A61K 2800/884* (2013.01); *A61K 2800/95* (2013.01)

(58) Field of Classification Search
CPC .. A61Q 5/065; A61K 8/8152; A61K 2800/43; A61K 8/41; A61K 2800/884; A61K 2800/882; A61K 8/89; A61K 8/8129; A61K 8/8188
USPC ...................................................... 8/558, 405
See application file for complete search history.

(56) References Cited

FOREIGN PATENT DOCUMENTS

| | | | |
|---|---|---|---|
| FR | 2 936 414 A1 | 4/2010 | |
| WO | WO 2016/066747 A | * 5/2016 | .............. A61K 8/58 |
| WO | WO 2016/066747 A1 | 5/2016 | |

OTHER PUBLICATIONS

STIC Search Report dated Aug. 14, 2020.*
International Search Report dated May 30, 2018 in PCT/EP2018/059049 filed on Apr. 9, 2018.

* cited by examiner

*Primary Examiner* — Eisa B Elhilo
(74) *Attorney, Agent, or Firm* — Oblon, McClelland, Maier & Neustadt, L.L.P.

(57) ABSTRACT

The invention relates to a hair dyeing process comprising: the application to the hair of a composition comprising a maleic anhydride ethylenic polymer and of an amine compound chosen from polyamine compounds bearing several primary amine and/or secondary amine groups and amino alkoxysilanes, and of at least one pigment the ethylenic polymer being derived from the polymerization of: (a) 45% to 95% by weight, relative to the total weight of monomers, of an ethylenic monomer bearing an at least Cs linear or branched alkyl group; (b) 5% to 25% by weight of maleic anhydride; (c) 0 to 50% by weight of additional monomer; the compositions used being anhydrous when the amine compound is an amino alkoxysilane.

33 Claims, No Drawings

HAIR DYEING PROCESS USING A PIGMENT, A MALEIC ANHYDRIDE ACRYLIC POLYMER AND AN AMINE COMPOUND

The present invention relates to a hair dyeing process using a pigment and a maleic anhydride acrylic polymer and an amine compound, and also to a kit for performing said process.

Cosmetic products often require the use of a film-forming polymer to obtain a deposit of the product on keratin materials that has good cosmetic properties. In particular, it is necessary for the film-forming deposit to have good persistence, in particular for the deposit not to transfer during contact with the fingers, clothing, and also good persistence on contact with water, especially rain or during showering or alternatively perspiration. Skin sebum may also damage the film-forming deposit.

In the field of dyeing of keratin fibres, it is already known practice to dye keratin fibres via various techniques using direct dyes for non-permanent dyeing or dye precursors for permanent dyeing.

Non-permanent dyeing or direct dyeing consists in dyeing keratin fibres with dye compositions containing direct dyes. These dyes are coloured and colouring molecules that have affinity for keratin fibres. They are applied to the keratin fibres for the time required to obtain the desired colouring, and are then rinsed out.

The standard dyes that are used are, in particular, dyes of the nitrobenzene, anthraquinone, nitropyridine, azo, xanthene, acridine, azine or triarylmethane type, or natural dyes.

Some of these dyes may be used under lightening conditions, which enables the production of colourings that are visible on dark hair.

It is also known practice to dye keratin fibres permanently via oxidation dyeing. This dyeing technique consists in applying to the keratin fibres a composition containing dye precursors such as oxidation bases and couplers. These precursors, under the action of an oxidizing agent, form one or more coloured substances in the hair.

The variety of molecules used as oxidation bases and couplers allows a wide range of colours to be obtained, and the colourings resulting therefrom are generally permanent, strong and resistant to external agents, especially to light, bad weather, washing, perspiration and rubbing.

In order to be visible on dark hair, these two dyeing techniques require prior or simultaneous bleaching of the keratin fibres. This bleaching step, performed with an oxidizing agent such as hydrogen peroxide or persalts, results in appreciable degradation of the keratin fibres, which impairs their cosmetic properties. The hair then has a tendency to become coarse, more difficult to disentangle and more brittle.

Another dyeing method consists in using pigments. Specifically, the use of pigment at the surface of the keratin fibres generally makes it possible to obtain visible colourings on dark hair, since the surface pigment masks the natural colour of the fibre. The use of pigment for dyeing keratin fibres is described, for example, in patent application FR 2 741 530, which recommends using for the temporary dyeing of keratin fibres a composition comprising at least one dispersion of film-forming polymer particles comprising at least one acid function and at least one pigment dispersed in the continuous phase of said dispersion.

The colourings obtained via this dyeing method have the drawback of being removed from the very first shampoo wash.

It is moreover known practice from patent application FR 2 907 678 to perform coloured coating of the hair using a composition comprising a polysiloxane/polyurea block copolymer and a pigment. However, with such a composition, the coatings obtained are not always very homogeneous and the individualization of the hair strands is not always very good.

It is also known practice from patent EP 1 392 222 to use a cosmetic composition for caring for and/or treating keratin materials, comprising a supramolecular polymer bearing a polymer backbone and at least two groups that are capable of forming at least three hydrogen bonds, and from patent EP 1 435 900 to use a hair composition comprising a supramolecular polymer comprising a polymer backbone and at least two groups that are capable of forming at least three hydrogen bonds and a surfactant or hair-conditioning agent. Thus, the aim of the present invention is to provide a composition for dyeing keratin fibres, such as the hair, which can produce coloured coatings that show good resistance to attacking factors such as brushing, do not leach, are resistant to sweat, light and bad weather, and are persistent with respect to shampooing and the various attacking factors to which the hair may be subjected, without degradation of the keratin fibres and while at the same time conserving perfectly individualized hair strands.

The inventors have discovered that a hair dyeing process using one or more pigments and a particular maleic anhydride ethylenic polymer combined with a particular amine compound makes it possible to obtain resistant hair dyeing.

The process in accordance with the present invention can produce on keratin fibres coloured coatings that can produce a visible colouring on all hair types, especially on dark hair, in a manner that is persistent with respect to shampooing, while at the same time preserving the physical qualities of the keratin fibre. Such a coating is in particular resistant to the external attacking factors to which the hair may be subjected such as blow drying and perspiration. It can in particular produce a smooth and homogeneous deposit. Moreover, it has been observed, surprisingly, that the hair strands remained perfectly individualized and could be styled without any problem.

The term "individualized hair strands" means hair strands which, after application of the composition and drying, are not stuck together (or are all separated from each other) and thus do not form clumps of hair, the coating being formed around virtually each hair strand.

The object of the present invention is a hair dyeing process comprising: the application to the hair of a composition comprising at least one pigment and a maleic anhydride ethylenic polymer and the application on the hair of an amine compound chosen from polyamine compounds containing several primary amine and/or secondary amine and/or amino alkoxysilane groups, the ethylenic polymer being derived from the polymerization of:

(a) 45% to 95% by weight, relative to the total weight of monomers, of an ethylenic monomer bearing an at least $C_8$ linear or branched alkyl group;

(b) 5% to 25% by weight of maleic anhydride;

(c) 0 to 50% by weight of additional monomer chosen from:

(i) polydimethylsiloxane silicone monomers bearing a mono(meth)acryloyloxy end group of formula (I) below;

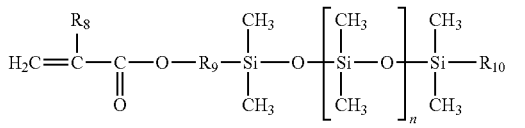
(I)

in which:
R$_8$ denotes a hydrogen atom or a methyl group;
R$_9$ denotes a linear or branched divalent hydrocarbon-based group containing from 1 to 10 carbon atoms and optionally containing one or two ether bond —O—;
R$_{10}$ denotes a linear or branched alkyl group containing from 1 to 10 carbon atoms and especially from 2 to 8 carbon atoms;
n denotes an integer ranging from 1 to 300;
(ii) linear or branched C$_1$-C$_6$ alkyl (meth)acrylate or C$_6$-C$_{12}$ cycloalkyl (meth)acrylate non-silicone monomers;
the compositions used being anhydrous when the amine compound is an amino alkoxysilane.

More precisely, the subject of the present invention is a hair dyeing process comprising: either the sequential application to the hair of a composition comprising a maleic anhydride ethylenic polymer and an amine compound chosen from polyamine compounds bearing several primary amine and/or secondary amine and amino alkoxysilane compounds, or a composition containing same,
or the application to the hair of a composition derived from the mixing of a composition comprising a maleic anhydride acrylic polymer and an amine compound chosen from amino alkoxysilanes, or a composition containing same, one and/or the other of the compositions comprising at least one pigment; and
the ethylenic polymer being as defined previously.

According to a first embodiment of the process according to the invention, a composition comprising an ethylenic polymer and an amine compound as defined previously, or a composition containing it and as defined previously, are applied sequentially to the hair, the compositions used being anhydrous when the amine compound is an amino alkoxysilane, and one and/or the other of the compositions comprising at least one pigment.

According to one embodiment of the process according to the invention, the composition comprising the ethylenic polymer is applied first to the hair, and said amine compound or a composition containing it is then applied, one and/or the other of the compositions comprising at least one pigment.

According to another embodiment, said amine compound, or a composition containing it, is applied first to the hair, and the composition comprising the ethylenic polymer is then applied, one and/or the other of the compositions comprising at least one pigment.

According to a second embodiment of the process according to the invention, a composition derived from the mixing (extemporaneous) of a composition comprising an ethylenic polymer as defined previously and of an amine compound, or of a composition containing it, as are defined previously, is applied to the hair, the composition derived from the mixing being anhydrous when the amine compound is an amino alkoxysilane, and one and/or the other of the compositions comprising at least one pigment.

According to one embodiment of the process according to the invention, the mixing of the composition comprising the ethylenic polymer and of the amine compound, or of the composition containing it, is performed in a time of between 1 minute and 24 hours before its application to the keratin materials, and preferably between 5 and 30 minutes.

The invention can be in a form of kit comprising a first composition comprising said maleic anhydride ethylenic polymer as described previously and a second composition comprising an amine compound as described previously and, the first and second compositions comprising at least one pigment and each being packaged in a separate packaging assembly, the compositions being anhydrous when the amine compound is an amino alkoxysilane.

The composition packaging assembly is, in a known manner, any packaging that is suitable for storing cosmetic compositions (in particular a bottle, tube, spray bottle or aerosol bottle).

The ethylenic polymer used according to the invention comprises an ethylenic monomer bearing an at least C$_8$ linear or branched alkyl group (referred to as a fatty-chain ethylenic monomer); said alkyl group may be a linear or branched C$_8$-C$_{22}$ or C$_8$ to C$_{12}$ alkyl group.

Such a fatty-chain ethylenic monomer may be chosen from:
a) linear or branched C$_8$-C$_{22}$ alkyl (meth)acrylates (i.e. comprising a C$_8$-C$_{22}$ alkyl group);
b) the (meth)acrylamides of formula CH$_2$=C(R$_1$)—CONR$_3$R$_4$ in which R$_1$ represents a hydrogen atom or a methyl radical, R$_3$ represents a hydrogen atom or a linear or branched C$_1$-C$_{12}$ alkyl group, and R$_4$ represents a linear or branched C$_8$ to C$_{12}$ alkyl group, such as an isooctyl, isononyl or undecyl group;
c) the vinyl esters of formula R$_5$—CO—O—CH=CH$_2$ in which R$_5$ represents a linear or branched C$_8$-C$_{22}$ alkyl group;
d) the ethers of formula R$_6$—O—CH=CH$_2$ in which R$_6$ represents a linear or branched C$_8$-C$_{22}$ alkyl group.

Linear or branched C$_8$-C$_{22}$ alkyl groups that may be mentioned include octyl, 2-ethylhexyl, isooctyl, nonyl, decyl, undecyl, lauryl, myristyl, palmityl, stearyl, eicosyl and behenyl radicals, and especially a 2-ethylhexyl, lauryl, behenyl or stearyl group.

Preferably, the fatty-chain ethylenic monomer is chosen from C$_8$-C$_{22}$ and especially C$_8$-C$_{18}$ alkyl (meth)acrylates, for instance 2-ethylhexyl acrylate, 2-ethylhexyl methacrylate, lauryl acrylate, lauryl methacrylate, behenyl acrylate, behenyl methacrylate, stearyl acrylate and stearyl methacrylate.

2-Ethylhexyl acrylate, 2-ethylhexyl methacrylate, stearyl acrylate or stearyl methacrylate is preferably used.

2-Ethylhexyl acrylate is preferentially used.

The fatty-chain monomer may be present in said ethylenic polymer in a content ranging from 45% to 90% by weight and preferably ranging from 50% to 90% by weight, relative to the total weight of monomers.

In the absence of additional monomer in the ethylenic polymer, the fatty-chain monomer may be present in a content ranging from 75% to 95% by weight, preferably ranging from 75% to 90% by weight and preferentially ranging from 78% to 87% by weight, relative to the total weight of monomers.

In the presence of additional monomer in the ethylenic polymer, the fatty-chain monomer may be present in a content ranging from 45% to 94.5% by weight, preferably ranging from 45% to 90% by weight, preferentially ranging from 50% to 75% by weight and more preferentially ranging from 52% to 67% by weight, relative to the total weight of monomers.

The ethylenic polymer used according to the invention contains maleic anhydride.

Maleic anhydride may be present in said ethylenic polymer in a content ranging from 10% to 25% by weight and preferably ranging from 13% to 22% by weight, relative to the total weight of monomers.

The additional silicone monomer is a polydimethylsiloxane bearing a mono(meth)acryloyloxy end group of formula (I) (referred to hereinbelow as a silicone monomer) below:

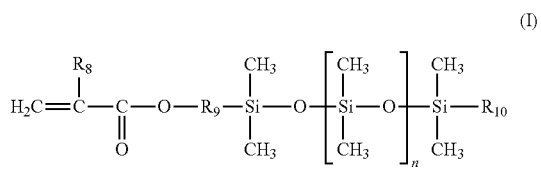

in which:
- $R_8$ denotes a hydrogen atom or a methyl group; preferably methyl;
- $R_9$ denotes a linear or branched, preferably linear, divalent hydrocarbon-based group containing from 1 to 10 carbon atoms, preferably containing from 2 to 4 carbon atoms, and optionally containing one or two —O— ether bonds; preferably an ethylene, propylene or butylene group;
- $R_{10}$ denotes a linear or branched alkyl group containing from 1 to 10 carbon atoms, especially from 2 to 8 carbon atoms; preferably methyl, ethyl, propyl, butyl or pentyl;
- n denotes an integer ranging from 1 to 300, preferably ranging from 3 to 200 and preferentially ranging from 5 to 100.

Use may be made in particular of monomethacryloyloxypropyl polydimethylsiloxanes such as those sold under the names MCR-M07, MCR-M17, MCR-M11 and MCR-M22 by Gelest Inc or the silicone macromonomers sold under the names X-22-2475, X-22-2426 and X-22-174DX by Shin-Etsu.

The additional silicone monomer may be present in said ethylenic polymer in a content ranging from 5% to 50% by weight, relative to the total weight of monomers, preferably ranging from 15% to 40% by weight, preferentially ranging from 20% to 35% by weight and especially ranging from 25% to 35% by weight.

The additional non-silicone monomer chosen from linear or branched $C_1$-$C_6$ alkyl (meth)acrylates may be, for example, methyl (meth)acrylate, ethyl (meth)acrylate, propyl (meth)acrylate, n-butyl (meth)acrylate, isobutyl (meth)acrylate, pentyl (meth)acrylate or hexyl (meth)acrylate. Methyl (meth)acrylate or ethyl (meth)acrylate is preferably used.

The $C_6$-$C_{12}$ cycloalkyl (meth)acrylate is preferably isobornyl (meth)acrylate.

The additional non-silicone monomer may be present in said ethylenic polymer in a content ranging from 0.5% to 50% by weight, relative to the total weight of monomers, preferably ranging from 5% to 50% by weight, preferentially ranging from 15% to 40% by weight and more preferentially ranging from 20% to 35% by weight.

According to one embodiment of the invention, the ethylenic polymer does not comprise any additional monomer: it is formed from ethylenic monomer bearing an at least $C_8$ linear or branched alkyl group and maleic anhydride.

According to another embodiment of the invention, the ethylenic polymer comprises at least one additional monomer as defined previously. The additional monomer may be present in said ethylenic polymer in a content ranging from 5% to 50% by weight, relative to the total weight of monomers, preferably ranging from 15% to 40% by weight, preferentially ranging from 20% to 35% by weight and especially ranging from 25% to 35% by weight.

According to another embodiment of the invention, the ethylenic polymer comprises at least one additional silicone monomer as defined previously.

According to another embodiment of the invention, the ethylenic polymer comprises at least one additional non-silicone monomer as defined previously. Preferably, it is a $C_6$-$C_{12}$ cycloalkyl (meth)acrylate.

According to another embodiment of the invention, the ethylenic polymer comprises at least one additional silicone monomer and at least one additional non-silicone monomer as defined previously.

According to a first embodiment of the invention, the ethylenic polymer comprises, or consists of:
(a) 75% to 95% by weight, relative to the total weight of monomers, of linear or branched $C_8$-$C_{22}$ alkyl (meth)acrylate;
(b) 5% to 25% by weight of maleic anhydride.

The ethylenic polymer especially comprises, or consists of:
(a) 75% to 95% by weight, relative to the total weight of monomers, of linear or branched $C_8$-$C_{18}$ alkyl (meth)acrylate;
(b) 5% to 25% by weight of maleic anhydride.

In particular, the ethylenic polymer comprises, or consists of:
(a) 75% to 95% by weight, relative to the total weight of monomers, of 2-ethylhexyl (meth)acrylate;
(b) 5% to 25% by weight of maleic anhydride.

In particular, the ethylenic polymer comprises, or consists of:
(a) 75% to 95% by weight, relative to the total weight of monomers, of stearyl (meth)acrylate;
(b) 5% to 25% by weight of maleic anhydride.

In particular, the ethylenic polymer comprises, or consists of:
(a) 75% to 95% by weight, relative to the total weight of monomers, of a mixture of 2-ethylhexyl (meth)acrylate and of stearyl (meth)acrylate;
(b) 5% to 25% by weight of maleic anhydride.

Preferably, the ethylenic polymer comprises, or consists of:
(a) 75% to 90% by weight, relative to the total weight of monomers, of linear or branched $C_8$-$C_{22}$ alkyl (meth)acrylate;
(b) 10% to 25% by weight of maleic anhydride.

The ethylenic polymer especially comprises, or consists of:
(a) 75% to 90% by weight, relative to the total weight of monomers, of linear or branched $C_8$-$C_{18}$ alkyl (meth)acrylate;
(b) 10% to 25% by weight of maleic anhydride.

In particular, the ethylenic polymer comprises, or consists of:
(a) 75% to 90% by weight, relative to the total weight of monomers, of 2-ethylhexyl (meth)acrylate;
(b) 10% to 25% by weight of maleic anhydride.

In particular, the ethylenic polymer comprises, or consists of:
(a) 75% to 90% by weight, relative to the total weight of monomers, of stearyl (meth)acrylate;
(b) 10% to 25% by weight of maleic anhydride.

In particular, the ethylenic polymer comprises, or consists of:
(a) 75% to 90% by weight, relative to the total weight of monomers, of a mixture of 2-ethylhexyl (meth)acrylate and of stearyl (meth)acrylate;
(b) 10% to 25% by weight of maleic anhydride.

Preferentially, the ethylenic polymer comprises, or consists of:
(a) 78% to 87% by weight, relative to the total weight of monomers, of linear or branched $C_8$-$C_{22}$ alkyl (meth)acrylate;
(b) 13% to 22% by weight of maleic anhydride.

The ethylenic polymer especially comprises, or consists of:
(a) 78% to 87% by weight, relative to the total weight of monomers, of linear or branched $C_8$-$C_{18}$ alkyl (meth)acrylate;
(b) 13% to 22% by weight of maleic anhydride.

In particular, the ethylenic polymer comprises, or consists of:
(a) 78% to 87% by weight, relative to the total weight of monomers, of 2-ethylhexyl (meth)acrylate;
(b) 13% to 22% by weight of maleic anhydride.

In particular, the ethylenic polymer comprises, or consists of:
(a) 78% to 87% by weight, relative to the total weight of monomers, of stearyl (meth)acrylate;
(b) 13% to 22% by weight of maleic anhydride.

In particular, the ethylenic polymer comprises, or consists of:
(a) 78% to 87% by weight, relative to the total weight of monomers, of a mixture of 2-ethylhexyl (meth)acrylate and of stearyl (meth)acrylate;
(b) 13% to 22% by weight of maleic anhydride.

The ethylenic polymer may be chosen from the following copolymers:
2-ethylhexyl acrylate/maleic anhydride (85/15 by weight)
2-ethylhexyl acrylate/maleic anhydride (80/20 by weight)
2-ethylhexyl acrylate/stearyl acrylate/maleic anhydride (50/30/20 by weight)

According to a second embodiment of the invention, the ethylenic polymer comprises, or consists of:
(a) 45% to 94.5% by weight, relative to the total weight of monomers, of linear or branched $C_8$-$C_{22}$ alkyl (meth)acrylate;
(b) 5% to 25% by weight of maleic anhydride;
(c) 0.5% to 50% by weight of silicone monomer (I) as described previously.

The ethylenic polymer especially comprises, or consists of:
(a) 45% to 94.5% by weight, relative to the total weight of monomers, of linear or branched $C_8$-$C_{18}$ alkyl (meth)acrylate;
(b) 5% to 25% by weight of maleic anhydride;
(c) 0.5% to 50% by weight of silicone monomer (I) as described previously.

In particular, the ethylenic polymer comprises, or consists of:
(a) 45% to 94.5% by weight, relative to the total weight of monomers, of 2-ethylhexyl (meth)acrylate;
(b) 5% to 25% by weight of maleic anhydride;
(c) 0.5% to 50% by weight of silicone monomer (I) as described previously.

In particular, the ethylenic polymer comprises, or consists of:
(a) 45% to 94.5% by weight, relative to the total weight of monomers, of stearyl (meth)acrylate;
(b) 5% to 25% by weight of maleic anhydride;
(c) 0.5% to 50% by weight of silicone monomer (I) as described previously.

In particular, the ethylenic polymer comprises, or consists of:
(a) 45% to 94.5% by weight, relative to the total weight of monomers, of a mixture of 2-ethylhexyl (meth)acrylate and of stearyl (meth)acrylate;
(b) 5% to 25% by weight of maleic anhydride;
(c) 0.5% to 50% by weight of silicone monomer (I) as described previously.

Preferably, the ethylenic polymer comprises, or consists of:
(a) 45% to 90% by weight, relative to the total weight of monomers, of linear or branched $C_8$-$C_{22}$ alkyl (meth)acrylate;
(b) 5% to 25% by weight of maleic anhydride;
(c) 5% to 50% by weight of silicone monomer (I) as described previously.

The ethylenic polymer especially comprises, or consists of:
(a) 45% to 90% by weight, relative to the total weight of monomers, of linear or branched $C_8$-$C_{18}$ alkyl (meth)acrylate;
(b) 5% to 25% by weight of maleic anhydride;
(c) 5% to 50% by weight of silicone monomer (I) as described previously.

In particular, the ethylenic polymer comprises, or consists of:
(a) 45% to 90% by weight, relative to the total weight of monomers, of 2-ethylhexyl (meth)acrylate;
(b) 5% to 25% by weight of maleic anhydride;
(c) 5% to 50% by weight of silicone monomer (I) as described previously.

In particular, the ethylenic polymer comprises, or consists of:
(a) 45% to 90% by weight, relative to the total weight of monomers, of stearyl (meth)acrylate;
(b) 5% to 25% by weight of maleic anhydride;
(c) 5% to 50% by weight of silicone monomer (I) as described previously.

In particular, the ethylenic polymer comprises, or consists of:
(a) 45% to 90% by weight, relative to the total weight of monomers, of a mixture of 2-ethylhexyl (meth)acrylate and of stearyl (meth)acrylate;
(b) 5% to 25% by weight of maleic anhydride;
(c) 5% to 50% by weight of silicone monomer (I) as described previously.

Preferentially, the ethylenic polymer comprises, or consists of:
(a) 50% to 75% by weight, relative to the total weight of monomers, of linear or branched $C_8$-$C_{22}$ alkyl (meth)acrylate;
(b) 10% to 25% by weight of maleic anhydride;
(c) 15% to 40% by weight of silicone monomer (I) as described previously.

The ethylenic polymer especially comprises, or consists of:
(a) 50% to 75% by weight, relative to the total weight of monomers, of linear or branched $C_8$-$C_{18}$ alkyl (meth)acrylate;
(b) 10% to 25% by weight of maleic anhydride;
(c) 15% to 40% by weight of silicone monomer (I) as described previously.

In particular, the ethylenic polymer comprises, or consists of:

(a) 50% to 75% by weight, relative to the total weight of monomers, of 2-ethylhexyl (meth)acrylate;
(b) 10% to 25% by weight of maleic anhydride;
(c) 15% to 40% by weight of silicone monomer (I) as described previously.

In particular, the ethylenic polymer comprises, or consists of:
(a) 50% to 75% by weight, relative to the total weight of monomers, of stearyl (meth)acrylate;
(b) 10% to 25% by weight of maleic anhydride;
(c) 15% to 40% by weight of silicone monomer (I) as described previously.

In particular, the ethylenic polymer comprises, or consists of:
(a) 50% to 75% by weight, relative to the total weight of monomers, of a mixture of 2-ethylhexyl (meth)acrylate and of stearyl (meth)acrylate;
(b) 10% to 25% by weight of maleic anhydride;
(c) 15% to 40% by weight of silicone monomer (I) as described previously.

More preferentially, the ethylenic polymer comprises, or consists of:
(a) 52% to 67% by weight, relative to the total weight of monomers, of linear or branched $C_8$-$C_{22}$ alkyl (meth)acrylate;
(b) 13% to 22% by weight of maleic anhydride;
(c) 20% to 35% by weight of silicone monomer (I) as described previously.

The ethylenic polymer especially comprises, or consists of:
(a) 52% to 67% by weight, relative to the total weight of monomers, of linear or branched $C_8$-$C_{18}$ alkyl (meth)acrylate;
(b) 13% to 22% by weight of maleic anhydride;
(c) 20% to 35% by weight of silicone monomer (I) as described previously.

In particular, the ethylenic polymer comprises, or consists of:
(a) 52% to 67% by weight, relative to the total weight of monomers, of 2-ethylhexyl (meth)acrylate;
(b) 13% to 22% by weight of maleic anhydride;
(c) 20% to 35% by weight of silicone monomer (I) as described previously.

In particular, the ethylenic polymer comprises, or consists of:
(a) 52% to 67% by weight, relative to the total weight of monomers, of stearyl (meth)acrylate;
(b) 13% to 22% by weight of maleic anhydride;
(c) 20% to 35% by weight of silicone monomer (I) as described previously.

In particular, the ethylenic polymer comprises, or consists of:
(a) 52% to 67% by weight, relative to the total weight of monomers, of a mixture of 2-ethylhexyl (meth)acrylate and of stearyl (meth)acrylate;
(b) 13% to 22% by weight of maleic anhydride;
(c) 20% to 35% by weight of silicone monomer (I) as described previously.

The ethylenic polymer may be chosen from the following copolymers:
2-ethylhexyl acrylate/maleic anhydride/silicone monomer (I)
stearyl acrylate/maleic anhydride/silicone monomer (I)
2-ethylhexyl acrylate/stearyl acrylate/maleic anhydride/silicone monomer (I)
in the respective monomer contents described previously, and in particular:
the 2-ethylhexyl acrylate/PDMS methacrylate/maleic anhydride copolymer (50/30/20 by weight).

According to a third embodiment of the invention, the ethylenic polymer comprises, or consists of:
(a) 45% to 94.5% by weight, relative to the total weight of monomers, of linear or branched $C_8$-$C_{22}$ alkyl (meth)acrylate;
(b) 5% to 25% by weight of maleic anhydride;
(c) 0.5% to 50% by weight of additional non-silicone monomer chosen from linear or branched $C_1$-$C_6$ alkyl (meth)acrylates or $C_6$-$C_{12}$ cycloalkyl (meth)acrylates.

The ethylenic polymer especially comprises, or consists of:
(a) 45% to 94.5% by weight, relative to the total weight of monomers, of linear or branched $C_8$-$C_{18}$ alkyl (meth)acrylate;
(b) 5% to 25% by weight of maleic anhydride;
(c) 0.5% to 50% by weight of $C_6$-$C_{12}$ cycloalkyl (meth)acrylate.

In particular, the ethylenic polymer comprises, or consists of:
(a) 45% to 94.5% by weight, relative to the total weight of monomers, of 2-ethylhexyl (meth)acrylate;
(b) 5% to 25% by weight of maleic anhydride;
(c) 0.5% to 50% by weight of isobornyl (meth)acrylate.

In particular, the ethylenic polymer comprises, or consists of:
(a) 45% to 94.5% by weight, relative to the total weight of monomers, of stearyl (meth)acrylate;
(b) 5% to 25% by weight of maleic anhydride;
(c) 0.5% to 50% by weight of isobornyl (meth)acrylate.

In particular, the ethylenic polymer comprises, or consists of:
(a) 45% to 94.5% by weight, relative to the total weight of monomers, of a mixture of 2-ethylhexyl (meth)acrylate and of stearyl (meth)acrylate;
(b) 5% to 25% by weight of maleic anhydride;
(c) 0.5% to 50% by weight of isobornyl (meth)acrylate.

Preferably, the ethylenic polymer comprises, or consists of:
(a) 45% to 90% by weight, relative to the total weight of monomers, of linear or branched $C_8$-$C_{22}$ alkyl (meth)acrylate;
(b) 5% to 25% by weight of maleic anhydride;
(c) 5% to 50% by weight of additional non-silicone monomer chosen from linear or branched $C_1$-$C_6$ alkyl (meth)acrylates or $C_6$-$C_{12}$ cycloalkyl (meth)acrylates.

The ethylenic polymer especially comprises, or consists of:
(a) 45% to 90% by weight, relative to the total weight of monomers, of linear or branched $C_8$-$C_{18}$ alkyl (meth)acrylate;
(b) 5% to 25% by weight of maleic anhydride;
(c) 5% to 50% by weight of $C_6$-$C_{12}$ cycloalkyl (meth)acrylate.

In particular, the ethylenic polymer comprises, or consists of:
(a) 45% to 90% by weight, relative to the total weight of monomers, of 2-ethylhexyl (meth)acrylate;
(b) 5% to 25% by weight of maleic anhydride;
(c) 5% to 50% by weight of isobornyl (meth)acrylate.

In particular, the ethylenic polymer comprises, or consists of:
(a) 45% to 90% by weight, relative to the total weight of monomers, of stearyl (meth)acrylate;
(b) 5% to 25% by weight of maleic anhydride;
(c) 5% to 50% by weight of isobornyl (meth)acrylate.

In particular, the ethylenic polymer comprises, or consists of:
(a) 45% to 90% by weight, relative to the total weight of monomers, of a mixture of 2-ethylhexyl (meth)acrylate and of stearyl (meth)acrylate;
(b) 5% to 25% by weight of maleic anhydride;
(c) 5% to 50% by weight of isobornyl (meth)acrylate.

Preferentially, the ethylenic polymer comprises, or consists of:
(a) 50% to 75% by weight, relative to the total weight of monomers, of linear or branched $C_8$-$C_{22}$ alkyl (meth)acrylate;
(b) 10% to 25% by weight of maleic anhydride;
(c) 15% to 40% by weight of additional non-silicone monomer chosen from linear or branched $C_1$-$C_6$ alkyl (meth)acrylates or $C_6$-$C_{12}$ cycloalkyl (meth)acrylates.

The ethylenic polymer especially comprises, or consists of:
(a) 50% to 75% by weight, relative to the total weight of monomers, of linear or branched $C_8$-$C_{18}$ alkyl (meth)acrylate;
(b) 10% to 25% by weight of maleic anhydride;
(c) 15% to 40% by weight of $C_6$-$C_{12}$ cycloalkyl (meth)acrylate.

In particular, the ethylenic polymer comprises, or consists of:
(a) 50% to 75% by weight, relative to the total weight of monomers, of 2-ethylhexyl (meth)acrylate;
(b) 10% to 25% by weight of maleic anhydride;
(c) 15% to 40% by weight of isobornyl (meth)acrylate.

In particular, the ethylenic polymer comprises, or consists of:
(a) 50% to 75% by weight, relative to the total weight of monomers, of stearyl (meth)acrylate;
(b) 10% to 25% by weight of maleic anhydride;
(c) 15% to 40% by weight of isobornyl (meth)acrylate.

In particular, the ethylenic polymer comprises, or consists of:
(a) 50% to 75% by weight, relative to the total weight of monomers, of a mixture of 2-ethylhexyl (meth)acrylate and of stearyl (meth)acrylate;
(b) 10% to 25% by weight of maleic anhydride;
(c) 15% to 40% by weight of isobornyl (meth)acrylate.

More preferentially, the ethylenic polymer comprises, or consists of:
(a) 52% to 67% by weight, relative to the total weight of monomers, of linear or branched $C_8$-$C_{22}$ alkyl (meth)acrylate;
(b) 13% to 22% by weight of maleic anhydride;
(c) 20% to 35% by weight of additional non-silicone monomer chosen from linear or branched $C_1$-$C_6$ alkyl (meth)acrylates or $C_6$-$C_{12}$ cycloalkyl (meth)acrylates.

The ethylenic polymer especially comprises, or consists of:
(a) 52% to 67% by weight, relative to the total weight of monomers, of linear or branched $C_8$-$C_{18}$ alkyl (meth)acrylate;
(b) 13% to 22% by weight of maleic anhydride;
(c) 20% to 35% by weight of $C_6$-$C_{12}$ cycloalkyl (meth)acrylate.

In particular, the ethylenic polymer comprises, or consists of:
(a) 52% to 67% by weight, relative to the total weight of monomers, of 2-ethylhexyl (meth)acrylate;
(b) 13% to 22% by weight of maleic anhydride;
(c) 20% to 35% by weight of isobornyl (meth)acrylate.

In particular, the ethylenic polymer comprises, or consists of:
(a) 52% to 67% by weight, relative to the total weight of monomers, of stearyl (meth)acrylate;
(b) 13% to 22% by weight of maleic anhydride;
(c) 20% to 35% by weight of isobornyl (meth)acrylate.

In particular, the ethylenic polymer comprises, or consists of:
(a) 52% to 67% by weight, relative to the total weight of monomers, of a mixture of 2-ethylhexyl (meth)acrylate and of stearyl (meth)acrylate;
(b) 13% to 22% by weight of maleic anhydride;
(c) 20% to 35% by weight of isobornyl (meth)acrylate.

The ethylenic polymer may be chosen from the following copolymers:
2-ethylhexyl acrylate/maleic anhydride/isobornyl (meth)acrylate
stearyl acrylate/maleic anhydride/isobornyl (meth)acrylate
2-ethylhexyl acrylate/stearyl acrylate/maleic anhydride/isobornyl (meth)acrylate
in the respective monomer contents described previously.

According to a fourth embodiment of the invention, the ethylenic polymer comprises, or consists of:
(a) 45% to 94.5% by weight, relative to the total weight of monomers, of linear or branched $C_8$-$C_{22}$ alkyl (meth)acrylate;
(b) 5% to 25% by weight of maleic anhydride;
(c) 0.5% to 50% by weight of a mixture of additional non-silicone monomer chosen from $C_6$-$C_{12}$ cycloalkyl (meth)acrylates and of silicone monomer (I) as described previously.

The ethylenic polymer especially comprises, or consists of:
(a) 45% to 94.5% by weight, relative to the total weight of monomers, of linear or branched $C_8$-$C_{18}$ alkyl (meth)acrylate;
(b) 5% to 25% by weight of maleic anhydride;
(c) 0.5% to 50% by weight of a mixture of $C_6$-$C_{12}$ cycloalkyl (meth)acrylate and of silicone monomer (I) as described previously.

In particular, the ethylenic polymer comprises, or consists of:
(a) 45% to 94.5% by weight, relative to the total weight of monomers, of 2-ethylhexyl (meth)acrylate;
(b) 5% to 25% by weight of maleic anhydride;
(c) 0.5% to 50% by weight of a mixture of isobornyl (meth)acrylate and of silicone monomer (I) as described previously.

In particular, the ethylenic polymer comprises, or consists of:
(a) 45% to 94.5% by weight, relative to the total weight of monomers, of stearyl (meth)acrylate;
(b) 5% to 25% by weight of maleic anhydride;
(c) 0.5% to 50% by weight of a mixture of isobornyl (meth)acrylate and of silicone monomer (I) as described previously.

In particular, the ethylenic polymer comprises, or consists of:
(a) 45% to 94.5% by weight, relative to the total weight of monomers, of a mixture of 2-ethylhexyl (meth)acrylate and of stearyl (meth)acrylate;
(b) 5% to 25% by weight of maleic anhydride;
(c) 0.5% to 50% by weight of a mixture of isobornyl (meth)acrylate and of silicone monomer (I) as described previously.

Preferably, the ethylenic polymer comprises, or consists of:

(a) 45% to 90% by weight, relative to the total weight of monomers, of linear or branched $C_8$-$C_{22}$ alkyl (meth)acrylate;
(b) 5% to 25% by weight of maleic anhydride;
(c) 5% to 50% by weight of a mixture of additional non-silicone monomer chosen from linear or branched $C_1$-$C_6$ alkyl (meth)acrylates or $C_6$-$C_{12}$ cycloalkyl (meth)acrylates and of silicone monomer (I) as described previously.

The ethylenic polymer especially comprises, or consists of:
(a) 45% to 90% by weight, relative to the total weight of monomers, of linear or branched $C_8$-$C_{18}$ alkyl (meth)acrylate;
(b) 5% to 25% by weight of maleic anhydride;
(c) 5% to 50% by weight of a mixture of $C_6$-$C_{12}$ cycloalkyl (meth)acrylate and of silicone monomer (I) as described previously.

In particular, the ethylenic polymer comprises, or consists of:
(a) 45% to 90% by weight, relative to the total weight of monomers, of 2-ethylhexyl (meth)acrylate;
(b) 5% to 25% by weight of maleic anhydride;
(c) 5% to 50% by weight of a mixture of isobornyl (meth)acrylate and of silicone monomer (I) as described previously.

In particular, the ethylenic polymer comprises, or consists of:
(a) 45% to 90% by weight, relative to the total weight of monomers, of stearyl (meth)acrylate;
(b) 5% to 25% by weight of maleic anhydride;
(c) 5% to 50% by weight of a mixture of isobornyl (meth)acrylate and of silicone monomer (I) as described previously.

In particular, the ethylenic polymer comprises, or consists of:
(a) 45% to 90% by weight, relative to the total weight of monomers, of a mixture of 2-ethylhexyl (meth)acrylate and of stearyl (meth)acrylate;
(b) 5% to 25% by weight of maleic anhydride;
(c) 5% to 50% by weight of a mixture of isobornyl (meth)acrylate and of silicone monomer (I) as described previously.

Preferentially, the ethylenic polymer comprises, or consists of:
(a) 50% to 75% by weight, relative to the total weight of monomers, of linear or branched $C_8$-$C_{22}$ alkyl (meth)acrylate;
(b) 10% to 25% by weight of maleic anhydride;
(c) 15% to 40% by weight of a mixture of additional non-silicone monomer chosen from linear or branched $C_1$-$C_6$ alkyl (meth)acrylates or $C_6$-$C_{12}$ cycloalkyl (meth)acrylates and of silicone monomer (I) as described previously.

The ethylenic polymer especially comprises, or consists of:
(a) 50% to 75% by weight, relative to the total weight of monomers, of linear or branched $C_8$-$C_{18}$ alkyl (meth)acrylate;
(b) 10% to 25% by weight of maleic anhydride;
(c) 15% to 40% by weight of a mixture of $C_6$-$C_{12}$ cycloalkyl (meth)acrylate and of silicone monomer (I) as described previously.

In particular, the ethylenic polymer comprises, or consists of:
(a) 50% to 75% by weight, relative to the total weight of monomers, of 2-ethylhexyl (meth)acrylate;
(b) 10% to 25% by weight of maleic anhydride;
(c) 15% to 40% by weight of a mixture of isobornyl (meth)acrylate and of silicone monomer (I) as described previously.

In particular, the ethylenic polymer comprises, or consists of:
(a) 50% to 75% by weight, relative to the total weight of monomers, of stearyl (meth)acrylate;
(b) 10% to 25% by weight of maleic anhydride;
(c) 15% to 40% by weight of a mixture of isobornyl (meth)acrylate and of silicone monomer (I) as described previously.

In particular, the ethylenic polymer comprises, or consists of:
(a) 50% to 75% by weight, relative to the total weight of monomers, of a mixture of 2-ethylhexyl (meth)acrylate and of stearyl (meth)acrylate;
(b) 10% to 25% by weight of maleic anhydride;
(c) 15% to 40% by weight of a mixture of isobornyl (meth)acrylate and of silicone monomer (I) as described previously.

More preferentially, the ethylenic polymer comprises, or consists of:
(a) 52% to 67% by weight, relative to the total weight of monomers, of linear or branched $C_8$-$C_{22}$ alkyl (meth)acrylate;
(b) 13% to 22% by weight of maleic anhydride;
(c) 20% to 35% by weight of a mixture of additional non-silicone monomer chosen from linear or branched $C_1$-$C_6$ alkyl (meth) acrylates or $C_6$-$C_{12}$ cycloalkyl (meth) acrylates and of silicone monomer (I) as described previously.

The ethylenic polymer especially comprises, or consists of:
(a) 52% to 67% by weight, relative to the total weight of monomers, of linear or branched $C_8$-$C_{18}$ alkyl (meth)acrylate;
(b) 13% to 22% by weight of maleic anhydride;
(c) 20% to 35% by weight of a mixture of $C_6$-$C_{12}$ cycloalkyl (meth)acrylate and of silicone monomer (I) as described previously.

In particular, the ethylenic polymer comprises, or consists of:
(a) 52% to 67% by weight, relative to the total weight of monomers, of 2-ethylhexyl (meth)acrylate;
(b) 13% to 22% by weight of maleic anhydride;
(c) 20% to 35% by weight of a mixture of isobornyl (meth)acrylate and of silicone monomer (I) as described previously.

In particular, the ethylenic polymer comprises, or consists of:
(a) 52% to 67% by weight, relative to the total weight of monomers, of stearyl (meth)acrylate;
(b) 13% to 22% by weight of maleic anhydride;
(c) 20% to 35% by weight of a mixture of isobornyl (meth)acrylate and of silicone monomer (I) as described previously.

In particular, the ethylenic polymer comprises, or consists of:
(a) 52% to 67% by weight, relative to the total weight of monomers, of a mixture of 2-ethylhexyl (meth)acrylate and of stearyl (meth)acrylate;
(b) 13% to 22% by weight of maleic anhydride;
(c) 20% to 35% by weight of a mixture of isobornyl (meth)acrylate and of silicone monomer (I) as described previously.

The ethylenic polymer may be chosen from the following copolymers:

2-ethylhexyl acrylate/maleic anhydride/isobornyl (meth)acrylate/silicone monomer (I)
stearyl acrylate/maleic anhydride/isobornyl (meth)acrylate/silicone monomer (I)
2-ethylhexyl acrylate/stearyl acrylate/maleic anhydride/isobornyl (meth)acrylate/silicone monomer (I)
in the respective monomer contents described previously.

Advantageously, the polymer used according to the invention consists of the monomers described previously.

Advantageously, the polymer used according to the invention is nonionic.

Preferably, the ethylenic polymer used according to the invention has a weight-average molecular weight ranging from 5000 to 1 000 000 g/mol, preferably ranging from 8000 to 500 000 g/mol and preferentially ranging from 10 000 to 350 000 g/mol.

The molecular weight may especially be determined by steric exclusion chromatography, with THF eluent, polystyrene standard, 2414 refractometric detector from Waters.

The copolymer may be a random, alternating (block) or gradient polymer. Preferably, the copolymer is random.

The copolymer used according to the invention may be prepared by radical polymerization of the monomers described previously, especially as a mixture or added sequentially during the polymerization, especially using an organic solvent with a boiling point of greater than or equal to 60° C., for instance isododecane, ethanol, ethyl acetate, tetrahydrofuran, methyltetrahydrofuran or methyl ethyl ketone. The organic solvent makes it possible to dissolve the monomers used and the polymer formed.

The polymerization is especially performed in the presence of a radical initiator especially of peroxide type (for example tert-butyl peroxy-2-ethylhexanoate: Trigonox 21S; 2,5-dimethyl-2,5-bis(2-ethylhexanoylperoxy)hexane: Trigonox 141; tert-butyl peroxypivalate: Trigonox 25C75 from AkzoNobel) or of azo type, for example (AIBN: azobisisobutyronitrile; V50: 2,2'-azobis(2-amidinopropane) dihydrochloride).

The polymerization may be performed at a temperature ranging from 60 to 100° C., and preferably ranging from 60 to 85° C.

The polymerization time may be about 24 hours.

A subject of the invention is also the novel polymers derived from the polymerization of:
(a) 45% to 94.5% by weight, relative to the total weight of monomers, of linear or branched $C_8$-$C_{22}$ alkyl (meth)acrylate;
(b) 5% to 25% by weight of maleic anhydride monomer;
(c) 0.5% to 50% by weight of additional monomer chosen from:
(i) polydimethylsiloxane silicone monomers bearing a mono(meth)acryloyloxy end group as defined previously;
(ii) linear or branched $C_1$-$C_6$ alkyl (meth)acrylate or $C_6$-$C_{12}$ cycloalkyl (meth)acrylate non-silicone monomers;
and also similar polymers with the following preferred contents:
(a) 75% to 95% and (b) 5% to 25%; (a) 75% to 90% and (b) 10% to 25%; (a) 78% to 87% and (b) 13% to 22%;
(a) 45% to 94.5% and (b) 5% to 25% and (c) 0.5% to 50%;
(a) 45% to 90% and (b) 5% to 25% and (c) 5% to 50%; (a) 50% to 75% and (b) 10% to 25% and (c) 15% to 40%; (a) 52% to 67% and (b) 13% to 22% and (c) 20% to 35%.

A subject of the invention is also the novel polymers described previously as second, third and fourth embodiments.

A subject of the invention is also the novel polymers derived from the polymerization of:

(a) 45% to 95% by weight, relative to the total weight of monomers, of an ethylenic monomer bearing an at least $C_8$ linear or branched alkyl group chosen from:
i) the (meth)acrylamides of formula $CH_2$=$C(R_1)$—$CONR_3R_4$ in which $R_1$ represents a hydrogen atom or a methyl radical, $R_3$ represents a hydrogen atom or a linear or branched $C_1$-$C_{12}$ alkyl group, and $R_4$ represents a linear or branched $C_8$ to $C_{12}$ alkyl group, such as an isooctyl, isononyl or undecyl group;
ii) the vinyl esters of formula $R_5$—CO—O—CH=$CH_2$ in which $R_5$ represents a linear or branched $C_8$-$C_{22}$ alkyl group;
iii) the ethers of formula $R_6$—O—CH=$CH_2$ in which $R_6$ represents a linear or branched $C_8$-$C_{22}$ alkyl group;
(b) 5% to 25% by weight of maleic anhydride monomer;
(c) 0% to 50% by weight of additional monomer chosen from:
(i) linear or branched $C_1$-$C_6$ alkyl (meth)acrylate or $C_6$-$C_{12}$ cycloalkyl (meth)acrylate non-silicone monomers; or
(ii) polydimethylsiloxane silicone monomers bearing a mono(meth)acryloyloxy end group as defined previously;
and also similar polymers with the following preferred contents:
a) 75% to 95% and (b) 5% to 25%; (a) 75% to 90% and (b) 10% to 25%; (a) 78% to 87% and (b) 13% to 22%;
(a) 45% to 94.5% and (b) 5% to 25% and (c) 0.5% to 50%;
(a) 45% to 90% and (b) 5% to 25% and (c) 5% to 50%; (a) 50% to 75% and (b) 10% to 25% and (c) 15% to 40%; (a) 52% to 67% and (b) 13% to 22% and (c) 20% to 35%.

The ethylenic polymer as defined previously may be present in the composition used according to the invention in a content ranging from 0.1% to 40% by weight, relative to the total weight of the composition, preferably from 0.5% to 35% by weight of active material, preferentially ranging from 1% to 30% by weight, and more preferentially ranging from 10% to 30% by weight.

Pigments

The composition that is useful in the process of the invention comprises at least one pigment. The term "pigment" means any pigment that gives colour to keratin materials. Their solubility in water at 25° C. and atmospheric pressure (760 mmHg) is less than 0.05% by weight, preferably less than 0.01%.

The pigments that may be used are chosen especially from the organic and/or mineral pigments known in the art, especially those described in Kirk-Othmer's chemical technology Encyclopaedia and in Ullmann's industrial chemistry encyclopaedia.

These pigments may be in the form of powder or of pigmentary paste. They may be coated or uncoated.

The pigments may be chosen, for example, from mineral pigments, organic pigments, lakes, pigments with special effects such as nacres or glitter flakes, and mixtures thereof.

The pigment may be a mineral pigment. The term "mineral pigment" means any pigment that satisfies the definition in Ullmann's encyclopaedia in the chapter on inorganic pigments. Among the mineral pigments that are useful in the present invention, mention may be made of iron oxides, chromium oxides, manganese violet, ultramarine blue, chromium hydrate, ferric blue and titanium oxide.

The pigment may be an organic pigment. The term "organic pigment" means any pigment that satisfies the definition in Ullmann's encyclopaedia in the chapter on organic pigments. The organic pigment may be chosen especially from nitroso, nitro, azo, xanthene, quinoline, anthraquinone, phthalocyanin, metal-complex, isoindolinone, isoindoline, quinacridone, perinone, perylene, diketopyrrolopyrrole, thioindigo, dioxazine, triphenylmethane and quinophthalone compounds.

In particular, the white or coloured organic pigments may be chosen from carmine, carbon black, aniline black, azo yellow, quinacridone, phthalocyanin blue, sorghum red, the blue pigments codified in the Color Index under the references CI 42090, 69800, 69825, 73000, 74100 and 74160, the yellow pigments codified in the Color Index under the references CI 11680, 11710, 15985, 19140, 20040, 21100, 21108, 47000 and 47005, the green pigments codified in the Color Index under the references CI 61565, 61570 and 74260, the orange pigments codified in the Color Index under the references CI 11725, 15510, 45370 and 71105, the red pigments codified in the Color Index under the references CI 12085, 12120, 12370, 12420, 12490, 14700, 15525, 15580, 15620, 15630, 15800, 15850, 15865, 15880, 17200, 26100, 45380, 45410, 58000, 73360, 73915 and 75470, and the pigments obtained by oxidative polymerization of indole or phenolic derivatives as described in patent FR 2 679 771.

The pigments in accordance with the invention may also be in the form of composite pigments as described in patent EP 1 184 426. These composite pigments may be compounds especially of particles comprising a mineral core, at least one binder for ensuring the binding of the organic pigments to the core, and at least one organic pigment at least partially covering the core.

The organic pigment may also be a lake. The term "lake" means dyes adsorbed onto insoluble particles, the assembly thus obtained remaining insoluble during use.

The inorganic substrates onto which the dyes are adsorbed are, for example, alumina, silica, calcium sodium borosilicate or calcium aluminium borosilicate, and aluminium.

Among the dyes, mention may be made of cochineal carmine. Mention may also be made of the dyes known under the following names: D&C Red 21 (CI 45 380), D&C Orange 5 (CI 45 370), D&C Red 27 (CI 45 410), D&C Orange 10 (CI 45 425), D&C Red 3 (CI 45 430), D&C Red 4 (CI 15 510), D&C Red 33 (CI 17 200), D&C Yellow 5 (CI 19 140), D&C Yellow 6 (CI 15 985), D&C Green (CI 61 570), D&C Yellow 10 (CI 77 002), D&C Green 3 (CI 42 053), D&C Blue 1 (CI 42 090).

An example of a lake that may be mentioned is the product known under the following name: D&C Red 7 (CI 15 850:1).

The pigment may also be a pigment with special effects. The term "pigments with special effects" means pigments that generally create a non-uniform coloured appearance (characterized by a certain shade, a certain vivacity and a certain lightness) that changes as a function of the conditions of observation (light, temperature, observation angles, etc.). They thus contrast with colored pigments that afford a standard uniform opaque, semi-transparent or transparent shade.

Several types of pigment with special effects exist: those with a low refractive index, such as fluorescent, photochromic or thermochromic pigments, and those with a higher refractive index, such as nacres or glitter flakes.

Examples of pigments with special effects that may be mentioned include nacreous pigments such as titanium mica coated with an iron oxide, mica coated with an iron oxide, mica coated with bismuth oxychloride, titanium mica coated with chromium oxide, titanium mica coated with an organic dye especially of the abovementioned type, and also nacreous pigments based on bismuth oxychloride. They may also be mica particles at the surface of which are superposed at least two successive layers of metal oxides and/or of organic dyestuffs.

The nacres may more particularly have a yellow, pink, red, bronze, orange, brown, gold and/or coppery colour or tint.

Nacres that may be used within the context of the present invention, by way of illustration, and that may especially be mentioned include the gold-coloured nacres sold especially by the company Engelhard under the name Gold 222C (Cloisonne), Sparkle gold (Timica), Gold 4504 (Chromalite) and Monarch gold 233X (Cloisonne); the bronze nacres sold especially by the company Merck under the name Bronze fine (17384) (Colorona) and Bronze (17353) (Colorona), by the company Eckart under the name Prestige Bronze and by the company Engelhard under the name Super bronze (Cloisonne); the orange nacres sold especially by the company Engelhard under the name Orange 363C (Cloisonne) and Orange MCR 101 (Cosmica) and by the company Merck under the name Passion orange (Colorona) and Matte orange (17449) (Microna); the brown nacres sold especially by the company Engelhard under the name Nu-antique copper 340XB (Cloisonne) and Brown CL4509 (Chromalite); the nacres with a copper tint sold especially by the company Engelhard under the name Copper 340A (Timica) and by the company Eckart under the name Prestige Copper; the nacres with a red tint sold especially by the company Merck under the name Sienna fine (17386) (Colorona); the nacres with a yellow tint sold especially by the company Engelhard under the name Yellow (4502) (Chromalite); the red nacres with a gold tint sold especially by the company Engelhard under the name Sunstone G012 (Gemtone); the black nacres with a gold tint sold especially by the company Engelhard under the name Nu antique bronze 240 AB (Timica), the blue nacres sold especially by the company Merck under the name Matte blue (17433) (Microna), Dark Blue (117324) (Colorona), the white nacres with a silvery tint sold especially by the company Merck under the name Xirona Silver, and the golden-green pink-orange nacres sold especially by the company Merck under the name Indian summer (Xirona), and mixtures thereof.

In addition to nacres on a mica support, multilayer pigments based on synthetic substrates such as alumina, silica, sodium calcium borosilicate or calcium aluminium borosilicate, and aluminium, may be envisaged.

Mention may also be made of pigments with an interference effect that are not fixed onto a substrate, for instance liquid crystals (Helicones HC from Wacker), holographic interference glitter flakes (Geometric Pigments or Spectra f/x from Spectratek). Pigments with special effects also comprise fluorescent pigments, whether these are substances that are fluorescent in daylight or that produce an ultraviolet fluorescence, phosphorescent pigments, photochromic pigments, thermochromic pigments and quantum dots, sold, for example, by the company Quantum Dots Corporation.

The variety of pigments that may be used in the present invention makes it possible to obtain a wide range of colours, and also particular optical effects such as metallic effects or interference effects.

The size of the pigment used in the cosmetic composition according to the present invention is generally between 10 nm and 200 µm, preferably between 20 nm and 80 µm and more preferentially between 30 nm and 50 µm.

The pigments may be dispersed in the product by means of a dispersant.

The dispersant serves to protect the dispersed particles against agglomeration or flocculation thereof. This dispersant may be a surfactant, an oligomer, a polymer or a mixture of several thereof, bearing one or more functionalities with strong affinity for the surface of the particles to be dispersed. In particular, they can physically or chemically attach to the surface of the pigments. These dispersants also contain at least one functional group that is compatible with or soluble in the continuous medium. In particular, 12-hydroxystearic acid esters and in particular 08 to 020 fatty acid esters of polyols such as glycerol or diglycerol are used, such as poly(12-hydroxystearic acid) stearate with a molecular weight of about 750 g/mol, such as the product sold under the name Solsperse 21 000 by the company Avecia, polyglyceryl-2 dipolyhydroxystearate (CTFA name) sold under the reference Dehymyls PGPH by the company Henkel, or polyhydroxystearic acid such as the product sold under the reference Arlacel P100 by the company Uniqema, and mixtures thereof.

As other dispersants that may be used in the compositions of the invention, mention may be made of quaternary ammonium derivatives of polycondensed fatty acids, for instance Solsperse 17 000 sold by the company Avecia, and polydimethylsiloxane/oxypropylene mixtures such as those sold by the company Dow Corning under the references DC2-5185 and DC2-5225 C.

The pigments that are used in the cosmetic composition according to the invention may be surface-treated with an organic agent.

Thus, the pigments that have been surface-treated beforehand, which are useful in the context of the invention, are pigments that have totally or partially undergone a surface treatment of chemical, electronic, electrochemical, mechanochemical or mechanical nature, with an organic agent such as those described especially in Cosmetics and Toiletries, February 1990, Vol. 105, pp. 53-64, before being dispersed in the composition in accordance with the invention. These organic agents may be chosen, for example, from amino acids; waxes, for example carnauba wax and beeswax; fatty acids, fatty alcohols and derivatives thereof, such as stearic acid, hydroxystearic acid, stearyl alcohol, hydroxystearyl alcohol and lauric acid and derivatives thereof; anionic surfactants; lecithins; sodium, potassium, magnesium, iron, titanium, zinc or aluminium salts of fatty acids, for example aluminium stearate or laurate; metal alkoxides; polysaccharides, for example chitosan, cellulose and derivatives thereof; polyethylene; (meth)acrylic polymers, for example polymethyl methacrylates; polymers and copolymers containing acrylate units; proteins; alkanolamines; silicone compounds, for example silicones, polydimethylsiloxanes, alkoxysilanes, alkylsilanes and siloxysilicates; organofluorine compounds, for example perfluoroalkyl ethers; fluorosilicone compounds.

The surface-treated pigments that are useful in the cosmetic composition according to the invention may also have been treated with a mixture of these compounds and/or may have undergone several surface treatments.

The surface-treated pigments that are useful in the context of the present invention may be prepared according to surface-treatment techniques that are well known to those skilled in the art, or may be commercially available in the required form.

Preferably, the surface-treated pigments are coated with an organic layer.

The organic agent with which the pigments are treated may be deposited on the pigments by evaporation of solvent, chemical reaction between the molecules of the surface agent or creation of a covalent bond between the surface agent and the pigments.

The surface treatment may thus be performed, for example, by chemical reaction of a surface agent with the surface of the pigments and creation of a covalent bond between the surface agent and the pigments or the fillers. This method is especially described in patent U.S. Pat. No. 4,578,266.

An organic agent covalently bonded to the pigments will preferably be used.

The agent for the surface treatment may represent from 0.1% to 50% by weight, preferably from 0.5% to 30% by weight and even more preferentially from 1% to 10% by weight relative to the total weight of the surface-treated pigments.

Preferably, the surface treatments of the pigments are chosen from the following treatments:
- a PEG-silicone treatment, for instance the AQ surface treatment sold by LCW;
- a chitosan treatment, for instance the CTS surface treatment sold by LCW;
- a triethoxycaprylylsilane treatment, for instance the AS surface treatment sold by LCW;
- a methicone treatment, for instance the SI surface treatment sold by LCW;
- a dimethicone treatment, for instance the Covasil 3.05 surface treatment sold by LCW;
- a dimethicone/trimethyl siloxysilicate treatment, for instance the Covasil 4.05 surface treatment sold by LCW;
- a lauroyllysine treatment, for instance the LL surface treatment sold by LCW;
- a lauroglysine dimethicone treatment, for instance the LL/SI surface treatment sold by LCW;
- a magnesium myristate treatment, for instance the MM surface treatment sold by LCW;
- an aluminium dimyristate treatment, for instance the MI surface treatment sold by Miyoshi;
- a perfluoropolymethylisopropyl ether treatment, for instance the FHC surface treatment sold by LCW;
- an isostearyl sebacate treatment, for instance the HS surface treatment sold by Miyoshi;
- a disodium stearoyl glutamate treatment, for instance the NAI surface treatment sold by Miyoshi;
- a dimethicone/disodium stearoyl glutamate treatment, for instance the SA/NAI surface treatment sold by Miyoshi;
- a perfluoroalkyl phosphate treatment, for instance the PF surface treatment sold by Daito;
- an acrylate/dimethicone copolymer and perfluoroalkyl phosphate treatment, for instance the FSA surface treatment sold by Daito;
- a polymethylhydrogen siloxane/perfluoroalkyl phosphate treatment, for instance the FSDI surface treatment sold by Daito;
- a lauryl lysine/aluminium tristearate treatment, for instance the LL-StAl surface treatment sold by Daito;
- an octyltriethylsilane treatment, for instance the OTS surface treatment sold by Daito;
- an octyltriethylsilane/perfluoroalkyl phosphate treatment, for instance the FOTS surface treatment sold by Daito;
- an acrylate/dimethicone copolymer treatment, for instance the ASC surface treatment sold by Daito;
- an isopropyl titanium triisostearate treatment, for instance the ITT surface treatment sold by Daito;
- a microcrystalline cellulose and carboxymethylcellulose treatment, for instance the AC surface treatment sold by Daito;

a cellulose treatment, for instance the C2 surface treatment sold by Daito;
an acrylate copolymer treatment, for instance the APD surface treatment sold by Daito;
a perfluoroalkyl phosphate/isopropyl titanium triisostearate treatment, for instance the PF+ITT surface treatment sold by Daito.

The composition in accordance with the present invention may moreover comprise one or more surface-untreated pigments.

According to a particular embodiment of the invention, the pigment(s) are mineral pigments.

According to another particular embodiment of the invention, the pigment(s) are chosen from nacres.

The amount of pigments may range from 0.5% to 40% and preferably from 1% to 20%.

The Amine Compounds

The amine compound used in the process according to the invention is especially an amine compound chosen from polyamine compounds bearing several primary amine and/or secondary amine groups or alternatively amino alkoxysilanes. It may thus be chosen from amino alkoxysilane compounds, diamine compounds and triamine compounds.

According to a first embodiment of the invention, polyamine compound is a compound comprising from 2 to 20 carbon atoms, in particular a non-polymeric compound. The term "non-polymeric compound" means a compound which is not directly obtained via a monomer polymerization reaction Polyamine compounds that may be mentioned include N-methyl-1,3-diaminopropane, N-propyl-1,3-diaminopropane, N-isopropyl-1,3-diaminopropane, N-cyclohexyl-1,3-diaminopropane, 2-(3-aminopropylamino)ethanol, 3-(2-aminoethyl)aminopropylamine, bis(3-aminopropyl)amine, methylbis(3-aminopropyl)amine, N-(3-aminopropyl)-1,4-diaminobutane, N,N-dimethyldipropylenetriamine, 1,2-bis(3-aminopropylamino)ethane, N,N'-bis(3-aminopropyl)-1,3-propanediamine, ethylenediamine, 1,3-propylenediamine, 1,4-butylenediamine, lysine, cystamine, xylenediamine, tris(2-aminoethyl)amine and spermidine. Preferably, the polyamine compound is chosen from ethylenediamine, 1,3-propylenediamine and 1,4-butylenediamine. Preferentially, the polyamine compound is ethylenediamine.

The amine compound may also be chosen from amino alkoxysilanes, such as those of formula (II):

$$R'_1Si(OR'_2)_z(R'_3)_x \quad (II)$$

in which:
R'$_1$ is a linear or branched, saturated or unsaturated, cyclic or acyclic $C_1$-$C_6$ hydrocarbon-based chain substituted with a group chosen from the following groups:
amine $NH_2$ or NHR with R=$C_1$-$C_4$ alkyl,
an aryl or aryloxy group substituted with an amino group or with a $C_1$-$C_4$ aminoalkyl group,
R'$_1$ possibly being interrupted in its chain with a heteroatom (O, S, NH) or a carbonyl group (CO), R'$_1$ being linked to the silicon atom directly via a carbon atom,
R'$_2$ and R'$_3$, which may be identical or different, represent a linear or branched alkyl group comprising from 1 to 6 carbon atoms,
z denotes an integer ranging from 1 to 3, and
x denotes an integer ranging from 0 to 2,
with z+x=3.

Preferably, R'$_2$ represents an alkyl group comprising from 1 to 4 carbon atoms.
Preferably, R'$_2$ represents a linear alkyl group, comprising from 1 to 4 carbon atoms.

Preferably, R'$_2$ represents an ethyl group.
Preferably, R'$_3$ represents an alkyl group comprising from 1 to 4 carbon atoms.
Preferably, R'$_3$ represents a linear alkyl group, comprising from 1 to 4 carbon atoms.
Preferably, R'$_3$ represents a methyl or ethyl group.
Preferably, R'$_1$ is an acyclic chain.
Preferably, R'$_1$ is a linear or branched, saturated or unsaturated $C_1$-$C_6$ hydrocarbon-based chain, substituted with an amine group $NH_2$ or NHR (R=$C_1$-$C_6$ alkyl, $C_3$-$C_6$ cycloalkyl or $C_6$ aromatic). Preferentially, R'$_1$ is a saturated linear $C_1$-$C_6$ hydrocarbon-based chain substituted with an amine group $NH_2$. More preferentially, R'$_1$ is a saturated linear $C_2$-$C_4$ hydrocarbon-based chain substituted with an amine group $NH_2$.
Preferably, R'$_1$ is a saturated linear $C_1$-$C_6$ hydrocarbon-based chain substituted with an amine group $NH_2$.
R'$_2$ represents an alkyl group comprising from 1 to 4 carbon atoms,
R'$_3$ represents an alkyl group comprising from 1 to 4 carbon atoms,
Preferably, z is equal to 3.
Preferably, the amino alkoxysilane of formula (II) is chosen from 3-aminopropyltriethoxysilane (APTES), 3-aminoethyltriethoxysilane (AETES), 3-aminopropylmethyldiethoxysilane, N-(2-aminoethyl)-3-aminopropyltriethoxysilane, 3-(m-aminophenoxy)propyltrimethoxysilane, p-aminophenyltrimethoxysilane and N-(2-aminoethylaminomethyl)phenethyltrimethoxysilane.
Preferably, the amino alkoxysilane (II) is chosen from 3-aminopropyltriethoxysilane (APTES), 3-aminoethyltriethoxysilane (AETES), 3-aminopropylmethyldiethoxysilane and N-(2-aminoethyl)-3-aminopropyltriethoxysilane.
Preferably, the amino alkoxysilane (II) is 3-aminopropyltriethoxysilane (APTES).
Preferably, the amine compound is chosen from 3-aminopropyltriethoxysilane (APTES), N-methyl-1,3-diaminopropane, N-propyl-1,3-diaminopropane, N-isopropyl-1,3-diaminopropane, N-cyclohexyl-1,3-diaminopropane, 2-(3-aminopropylamino)ethanol, 3-(2-aminoethyl)aminopropylamine, bis(3-aminopropyl)amine, methylbis(3-aminopropyl)amine, N-(3-aminopropyl)-1,4-diaminobutane, N,N-dimethyldipropylenetriamine, 1,2-bis(3-aminopropylamino)ethane, N,N'-bis(3-aminopropyl)-1,3-propanediamine, ethylenediamine, 1,3-propylenediamine, 1,4-butylenediamine and lysine.

Preferentially, the amine compound is chosen from ethylenediamine, 1,3-propylenediamine, 1,4-butylenediamine and 3-aminopropyltriethoxysilane (APTES). More preferentially, the amine compound is ethylenediamine or 3-aminopropyltriethoxysilane (APTES).

The amine compound may also be chosen from amine-based polymers, in particular having a weight-average molecular weight ranging from 500 to 1 000 000, preferably ranging from 500 to 500 000, and preferentially ranging from 500 to 100 000.

As amine-based polymer, use may be made of poly(($C_2$-$C_5$)alkyleneimines), and in particular polyethyleneimines and polypropyleneimines, especially poly(ethyleneimine)s (for example the product sold under the reference 46,852-3 by the company Aldrich Chemical); poly(allylamine) (for example the product sold under the reference 47,913-6 by the company Aldrich Chemical); polyvinylamines and copolymers thereof, in particular with vinylamides; mention may in particular be made of vinylamine/vinylformamide copolymers such as those sold under the name Lupamin® 9030 by the company BASF; polyamino acids bearing $NH_2$ groups, such as polylysine, for example the product sold by the company JNC Corporation (formerly Chisso); aminodextran, such as the product sold by the company CarboMer Inc; amino polyvinyl alcohol, such as the product sold by the company CarboMer Inc, acrylamidopropylamine-based copolymers; chitosans;
polydimethylsiloxanes comprising primary amine groups at the chain end or on side chains, for example aminopropyl side or end groups, for instance those of formula (A) or (B) or (C):

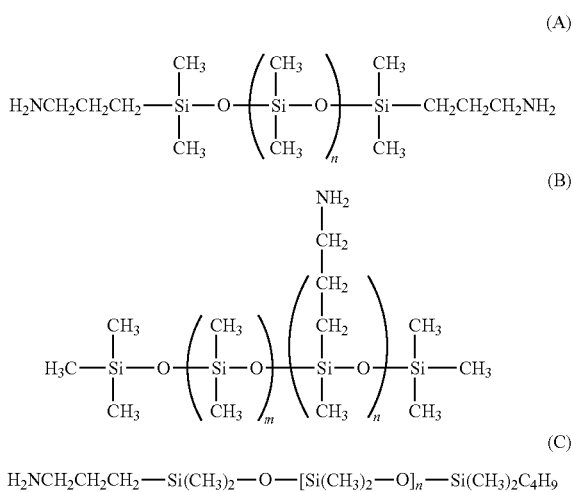

in formula (A): the value of n is such that the weight-average molecular weight of the silicone is between 500 and 55 000. As an example of aminosilicone (A), mention may be made of those sold under the names DMS-A11, DMS-A12, DMS-A15, DMS-A21, DMS-A31, DMS-A32 and DMS-A35 by the company Gelest;
in formula (B), the values of n and m are such that the weight-average molecular weight of the silicone is between 1000 and 55 000. As examples of silicone (B), mention may be made of those sold under the names AMS-132, AMS-152, AMS-162, AMS-163, AMS-191 and AMS-1203 by the company Gelest;
in formula (C), the value of n is such that the weight-average molecular weight of the silicone is between 500 and 3000. As an example of silicone (C), mention may be made of those sold under the names MCR-A11 and MCR-A12 by the company Gelest;
amodimethicones of formula (D):

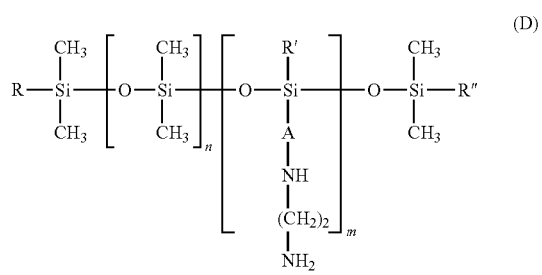

in which R, R' and R", which may be identical or different, each represent a $C_1$-$C_4$ alkyl or hydroxyl group, A represents a 03 alkylene group and m and n are such that the weight-average molecular mass of the compound is between 5000 and 500 000 approximately.

The polyether amines known especially under the reference Jeffamine® from the company Huntsman; and especially:

Polyethylene glycol and/or polypropylene glycol α,ω-diamines (bearing an amine function at the end of the chain), for instance the products sold under the names Jeffamine® D-230, D-400, D-2000, D-4000, ED-600, ED-9000, ED-2003;

Polytetrahydrofuran (or polytetramethylene glycol) α,ω-diamines;

polybutadiene α,ω-diamines;

Polyamidoamine (PANAM) dendrimers bearing amine end functions;

Poly(meth)acrylates or poly(meth)acrylamides bearing primary or secondary amine side functions, such as poly(3-aminopropyl)methacrylamide or poly(2-aminoethyl) methacrylate.

As amine-based polymer, use is preferably made of polydimethylsiloxanes comprising primary amine groups at the chain end or on side chains.

Preferentially, polydimethylsiloxanes comprising aminopropyl end groups at the chain end are used.

Advantageously, the polyamine compounds used in the process according to the invention are chosen from polydimethylsiloxanes comprising primary amine groups at the chain end or on side chains.

Preferentially, the amine compounds used in the process according to the invention are chosen from polydimethylsiloxanes comprising aminopropyl end groups at the chain end, 3-aminopropyltriethoxysilane (APTES).

When the compound is an amino alkoxysilane, the composition containing it is anhydrous.

The composition containing the ethylenic polymer, when it is intended to be mixed with the composition containing the amino alkoxysilane, is also anhydrous.

Advantageously, the amine compound used in the process according to the invention is used in a mole ratio of amine group of the amine compound/maleic anhydride group of the ethylenic polymer ranging from 0.01 to 10, preferably ranging from 0.1 to 5, preferentially ranging from 0.1 to 2 and more preferentially ranging from 0.1 to 1.

On contact with the ethylenic polymer, the polyamine compound reacts with the maleic anhydride functions to form a crosslinked polymer, for example in the following manner:

Scheme I

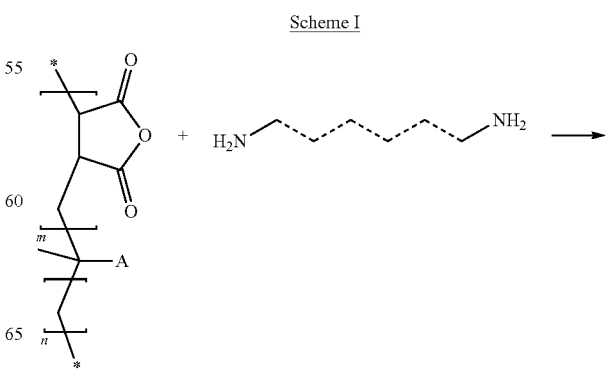

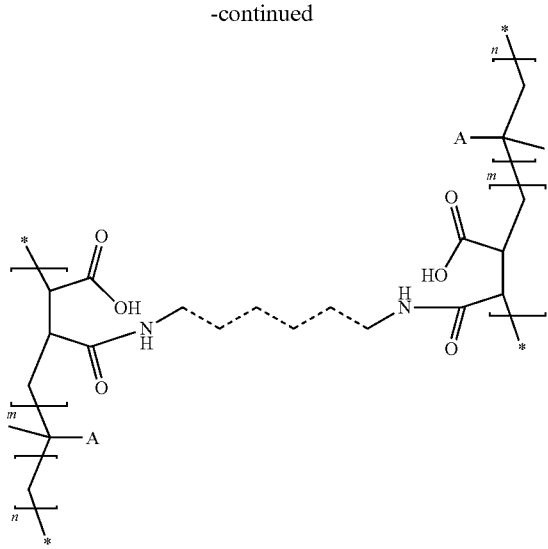

the unit bearing the group A symbolizing the unit derived from the fatty-chain ethylenic monomer.

Such a crosslinked polymer is novel and thus also forms the subject of the present invention.

The crosslinked polymer may thus be obtained by reacting said polyamine compound with the maleic anhydride acrylic polymer described previously. Some or all of the anhydride groups react with the NH or $NH_2$ group of the amine compound and form a unit bearing an amide group and a carboxylic acid group as described in scheme I.

The amino alkoxysilane (II) used in anhydrous medium reacts with the maleic anhydride group present in the polymer to form a unit having the following formula:

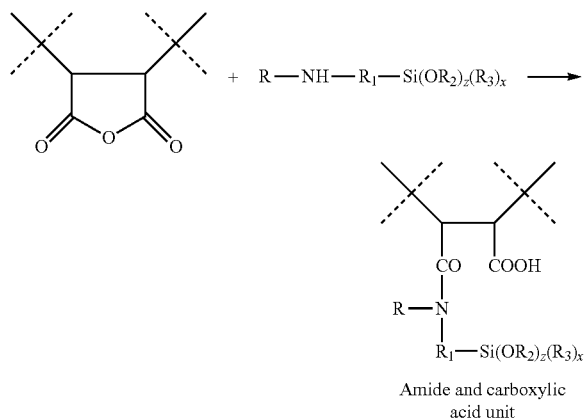

Amide and carboxylic acid unit

Such a polymer bearing an amino alkoxysilane group is novel and thus also forms the subject of the present invention. A subject of the invention is also an anhydrous composition comprising such a polymer bearing an amino alkoxysilane group and a physiologically acceptable medium.

The polymer bearing an amino alkoxysilane group may thus be obtained by reacting in anhydrous medium the amino alkoxysilane (II) with the maleic anhydride ethylenic polymer described previously. Some or all of the anhydride groups react with the NH group of compound (II) and form a unit bearing an amide group and a carboxylic acid group as described in scheme II.

According to one embodiment of the process according to the invention, a mixture, especially an extemporaneous mixture, of one or more pigments, of the ethylenic polymer and of an amino alkoxysilane (II) is prepared and the mixture is applied to the keratin materials. It is also possible to perform sequential application of, on the one hand, the ethylenic polymer and, on the other hand, an amino alkoxysilane (II) as are defined previously.

Hydrocarbon-Based Oil

According to a preferred embodiment of the invention, the composition comprising the ethylenic polymer may contain a hydrocarbon-based oil. More generally, the compositions used in the process according to the invention preferably comprise an oil, especially a hydrocarbon-based oil.

The hydrocarbon-based oil is an oil that is liquid at room temperature (25° C.).

The term "hydrocarbon-based oil" means an oil formed essentially from, or even constituted of, carbon and hydrogen atoms, and optionally oxygen and nitrogen atoms, and not containing any silicon or fluorine atoms. It may contain alcohol, ester, ether, carboxylic acid, amine and/or amide groups.

The hydrocarbon-based oil may be volatile or non-volatile.

The hydrocarbon-based oil may be chosen from:

hydrocarbon-based oils containing from 8 to 14 carbon atoms, and especially:
- branched $C_8$-$C_{14}$ alkanes, for instance $C_8$-$C_{14}$ isoalkanes of petroleum origin (also known as isoparaffins), for instance isododecane (also known as 2,2,4,4,6-pentamethylheptane), isodecane and, for example, the oils sold under the trade name Isopar or Permethyl,
- linear alkanes, for instance n-dodecane (C12) and n-tetradecane (C14) sold by Sasol under the respective references Parafol 12-97 and Parafol 14-97, and also mixtures thereof, the undecane-tridecane mixture, the mixtures of n-undecane (C11) and of n-tridecane (C13) obtained in Examples 1 and 2 of patent application WO 2008/155 059 from the company Cognis, and mixtures thereof, short-chain esters (containing from 3 to 8 carbon atoms in total) such as ethyl acetate, methyl acetate, propyl acetate or n-butyl acetate hydrocarbon-based oils of plant origin such as triglycerides constituted of fatty acid esters of glycerol, the fatty acids of which may have chain lengths varying from $C_4$ to $C_{24}$, these chains possibly being linear or branched, and saturated or unsaturated; these oils are especially heptanoic or octanoic acid triglycerides, or alternatively wheatgerm oil, sunflower oil, grapeseed oil, sesame seed oil, corn oil, apricot oil, castor oil, shea oil, avocado oil, olive oil, soybean oil, sweet almond oil, palm oil, rapeseed oil, cottonseed oil, hazelnut oil, macadamia oil, jojoba oil, alfalfa oil, poppy oil, pumpkin oil, marrow oil, blackcurrant oil, evening primrose oil, millet oil, barley oil, *quinoa* oil, rye oil, safflower oil, candlenut oil, passion-flower oil and musk rose oil; shea butter; or else caprylic/capric acid triglycerides, for instance those sold by the company Stéarineries Dubois or those sold under the names Miglyol 810®, 812® and 818® by the company Dynamit Nobel, synthetic ethers having from 10 to 40 carbon atoms;

linear or branched hydrocarbons of mineral or synthetic origin, such as petroleum jelly, polydecenes, hydrogenated polyisobutene such as Parleam®, squalane and liquid paraffins, and mixtures thereof, synthetic esters such as oils of formula $R_1COOR_2$ in which $R_1$ represents a linear or branched fatty acid residue containing from 1 to 40 carbon atoms and $R_2$ represents an, in particular branched, hydrocarbon-based chain containing from 1 to 40 carbon atoms, on the condition that $R_1+R_2 \geq 10$, for instance purcellin oil (cetostearyl octanoate), isopropyl myristate, isopropyl palmitate, $C_{12}$ to $C_{15}$ alkyl benzoates, hexyl laurate, diisopropyl adipate, isononyl isononanoate, 2-ethylhexyl palmitate, isostearyl isostearate, 2-hexyldecyl laurate, 2-octyldecyl palmitate, 2-octyldodecyl myristate, alkyl or polyalkyl heptanoates, octanoates, decanoates or ricinoleates such as propylene glycol dioctanoate; hydroxylated esters such as isostearyl lactate, diisostearyl malate and 2-octyldodecyl lactate; polyol esters and pentaerythritol esters, fatty alcohols that are liquid at room temperature, with a branched and/or unsaturated carbon-based chain containing from 12 to 26 carbon atoms, for instance octyldodecanol, isostearyl alcohol, oleyl alcohol, 2-hexyldecanol, 2-butyloctanol and 2-undecylpentadecanol.

Advantageously, the hydrocarbon-based oil is apolar (thus formed solely from carbon and hydrogen atoms).

The hydrocarbon-based oil is preferably chosen from hydrocarbon-based oils containing from 8 to 14 carbon atoms, in particular the apolar oils described previously.

Preferentially, the hydrocarbon-based oil is isododecane.

The composition comprising the polymer may contain, in addition to the hydrocarbon-based oil, a silicone oil. The term "silicone oil" means an oil comprising at least one silicon atom and especially at least one Si—O group. The silicone oil may be volatile or non-volatile.

The term "volatile oil" means an oil (or non-aqueous medium) that is capable of evaporating on contact with the skin in less than one hour, at room temperature and at atmospheric pressure. The volatile oil is a volatile cosmetic oil, which is liquid at room temperature, especially having a non-zero vapour pressure, at room temperature and atmospheric pressure, in particular having a vapour pressure ranging from 0.13 Pa to 40 000 Pa ($10^{-3}$ to 300 mmHg), preferably ranging from 1.3 Pa to 13 000 Pa (0.01 to 100 mmHg) and preferentially ranging from 1.3 Pa to 1300 Pa (0.01 to 10 mmHg).

The term "non-volatile oil" means an oil with a vapour pressure of less than 0.13 Pa.

Volatile silicone oils that may be mentioned include volatile linear or cyclic silicone oils, especially those with a viscosity $\leq 8$ centistokes (cSt) ($8 \times 10^{-6}$ m$^2$/s), and especially having from 2 to 10 silicon atoms and in particular from 2 to 7 silicon atoms, these silicones optionally comprising alkyl or alkoxy groups having from 1 to 10 carbon atoms. As volatile silicone oils that may be used in the invention, mention may be made especially of dimethicones with viscosities of 5 and 6 cSt, octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and mixtures thereof.

As non-volatile silicone oils, mention may be made of linear or cyclic non-volatile polydimethylsiloxanes (PDMSs); polydimethylsiloxanes comprising alkyl, alkoxy or phenyl groups, which are pendant or at the end of a silicone chain, these groups containing from 2 to 24 carbon atoms; phenyl silicones, for instance phenyl trimethicones, phenyl dimethicones, phenyltrimethylsiloxydiphenylsiloxanes, diphenyl dimethicones, diphenylmethyldiphenyltrisiloxanes and 2-phenylethyl trimethylsiloxysilicates.

Advantageously, the composition may comprise a hydrocarbon-based oil in a content ranging from 60% to 100% by weight relative to the total weight of the oils present in the composition and from 0 to 40% by weight of silicone oil. According to a preferred embodiment of the invention, the composition contains as oil only a hydrocarbon-based oil.

Advantageously, the composition comprises a non volatile oil, preferably a non volatile hydrocarbonated oil.

The composition according to the invention may comprise a cosmetic additive chosen from water, fragrances, preserving agents, fillers, UV-screening agents, oils, waxes, surfactants, moisturizers, vitamins, ceramides, antioxidants, free-radical scavengers, polymers, thickeners and dyestuffs.

The composition according to the invention may also comprise other dyestuffs such as liposoluble dyes or water-soluble dyes. This dyestuff may be present in a content ranging from 0.01% to 30% by weight, relative to the total weight of the composition.

The liposoluble dyes are, for example, Sudan Red, D&C Red 17, D&C Green 6, β-carotene, soybean oil, Sudan Brown, D&C Yellow 11, D&C Violet 2, D&C Orange 5, quinoline yellow and annatto. The water-soluble dyes are, for example, beetroot juice or methylene blue.

According to one embodiment, the composition according to the invention is an anhydrous composition. The term "anhydrous composition" means a composition containing less than 2% by weight of water, or even less than 0.5% of water, and is especially free of water. Where appropriate, such small amounts of water may especially be introduced by ingredients of the composition that may contain residual amounts thereof.

In particular, when the process according to the invention uses an amino alkoxysilane as described previously, the composition(s) used are advantageously anhydrous.

The invention is illustrated in greater detail in the examples that follow.

EXAMPLE 1: 2-ETHYLHEXYL ACRYLATE/MALEIC ANHYDRIDE COPOLYMER (85/15 BY WEIGHT)

170 g of 2-ethylhexyl acrylate and 30 g of maleic anhydride were placed in a jacketed 1-litre reactor equipped with a stirring anchor. A mixture of 210 g of isododecane and 90 g of ethyl acetate was then added.

The medium was brought to a temperature of 40° C. with stirring (150 rpm) and was sparged with argon for 10 minutes, followed by addition of 2 g of initiator tert-butyl peroxy-2-ethylhexanoate (Trigonox® 21S from AkzoNobel).

The heating of the jacket was set at 90° C. for 7 hours at 150 rpm.

The medium was then diluted with 300 g of isododecane, and then concentrated by distillation to remove the ethyl acetate and the unreacted maleic anhydride.

A solution containing 30% by weight of the copolymer in isododecane was finally obtained.

The polymer obtained has a molecular weight (Mw) of close to 12 000 g/mol.

EXAMPLE 2: 2-ETHYLHEXYL ACRYLATE/MALEIC ANHYDRIDE COPOLYMER (80/20 BY WEIGHT)

The polymer was prepared according to the procedure of Example 1, using 160 g of 2-ethylhexyl acrylate and 40 g of maleic anhydride.

A solution containing 32% by weight of the copolymer in isododecane (yield of greater than 90%) was finally obtained.

The polymer obtained has a molecular weight (Mw) of close to 15000 g/mol.

EXAMPLE 3: 2-ETHYLHEXYL ACRYLATE/PDMS METHACRYLATE*/MALEIC ANHYDRIDE COPOLYMER (50/30/20 BY WEIGHT)

The polymer was prepared according to the procedure of Example 1, using:
40 g of maleic anhydride with 28 g of isododecane and 21 g of ethyl acetate;
sparging with argon, followed by addition over 1 hour of a mixture of 100 g of 2-ethylhexyl acrylate, 60 g of PDMS methacrylate* (X-22-2426 from Shin-Etsu; size of the PDMS chain=12 000 g/mol), 168 g of isododecane, 72 g of ethyl acetate and 2 g of Trigonox® 21S.

A solution containing 40% by weight of the copolymer in isododecane was finally obtained.

EXAMPLE 4: 2-ETHYLHEXYL ACRYLATE/STEARYL ACRYLATE/MALEIC ANHYDRIDE COPOLYMER (50/30/20 BY WEIGHT)

The polymer was prepared according to the procedure of Example 1, using:
20 g of 2-ethylhexyl acrylate and 20 g of maleic anhydride;
40 g of maleic anhydride with 28 g of isododecane and 21 g of ethyl acetate;
sparging with argon, followed by addition over 1 hour of a mixture of 100 g of 2-ethylhexyl acrylate, 60 g of stearyl methacrylate, 168 g of isododecane, 72 g of ethyl acetate and 2 g of Trigonox® 21S.

A solution containing 41% by weight of the copolymer in isododecane was finally obtained.

The polymer obtained has a molecular weight (Mw) of close to 17 000 g/mol.

Preparation of the Dyeing Compositions
Invention 1:

A dyeing composition was prepared from a solution of the copolymer of example 1(2-Ethylhexyl acrylate/maleic anhydride copolymer (85/15) in isododecane (15% active material), 6% of pigment (MICA (and) IRON OXIDES) and qs to 100% with isododecane.

Comparison 1:

The following comparative composition was prepared with the same pigment used at the same concentration.

| Comparative composition 1 | Conc. |
|---|---|
| GLYCINE | 3% |
| PHENOXYETHANOL | 0.7% |
| DIVINYLDIMETHICONE/DIMETHICONE COPOLYMER (and) C12-13 PARETH-3 (and) C12-13 PARETH-23 (60% Active Material in an aqueous emulsion) | 8.3% |
| CAPRYLYL GLYCOL | 1% |
| MAGNESIUM ALUMINUM SILICATE | 1.1% |
| STYRENE/ACRYLATES/AMMONIUM METHACRYLATE COPOLYMER (and) SODIUM LAURETH SULFATE (and) CAPRYLYL GLYCOL (40% Active material in an aqueous emulsion 40%) | 21% |
| MICA (and) IRON OXIDES | 6% |
| water | q.s |

Comparison 2:

A comparative composition was prepared from a solution of 2-ethylhexyl acrylate co stearyl-methacrylate (80/20) in isododecane (33%)(15 active material in isododecane), 6% of pigment (MICA (and) IRON OXIDES) and qs 100% isododecane.

Evaluation of the Color Resistance

These dyeing compositions were applied on locks of natural hair with 90% of white hair. The compositions were applied on dried hair and on wet hair. 0.5 g of the dyeing composition was applied on 1 g of hair lock. After 24 h hours, the locks were rinsed with water and dried. Then the locks were shampooed and dried.

The color resistance was visually evaluated on washed dried hair and after 1 shampoo, 3 shampoos and 5 shampoos on dried hair according to a resistance evaluation scale ranging from 5 (high color resistance) to 1 (no color resistance).

The evaluation is summarized in the table below:

| | Application on | Water resistance | After 1 shampoo | After 3 shampoo | After 5 shampoo |
|---|---|---|---|---|---|
| Invention 1 | Dried hair | 5 | 5 | 4 | 2 |
| | Wet hair | 5 | 5 | 5 | 4 |
| Comparative comp. 1 | Dried hair | 5 | 5 | 2 | 1 |
| | Wet hair | 5 | 5 | 2 | 1 |
| Comparative comp. 2 | Dried hair | 5 | 5 | 2 | 1 |

These examples show that the composition of the invention provides an improvement of the color resistance to shampoos. After 5 shampoos, the color is still acceptable whereas with the comparative compositions 1 or 2, the locks are no more colored.

Two Step Process.

These dyeing compositions (invention 1 and Invention 2) were applied on locks of natural hair with 90% of white hair. The compositions were applied on dried hair. 0.5 g of the dyeing composition was applied on 1 g of hair lock. Then a solution containing an amino compounds was applied. After 24 h hours, the locks were rinsed with water and dried. Then the locks were shampooed and dried.

Invention 2:

A dyeing composition was prepared with a solution of a copolymer 2-EthylHexylacrylateacrylate-co-isobornyl acrylate-co-maleic anhydre (20/60/20) in isododecane, (15% of active material).

Invention 3:

the amino compound is APTES (3-aminopropyl)triethoxysilane (50 in isododecane.

Invention 4:

the amino compound is poly(dimethylsiloxane),bis(3-aminopropyl)terminated (PDMS-diNH2), Mn 25000 g/mol (50% in isododecane)

Invention 5:

the amino compound is BIS-CETEARYL AMODIMETHICONE (50% isododecane)

The evaluation conducted as disclosed above is summarized in the table below:

|  | Application on | Water resistance | After 1 shampoo | After 3 shampoo | After 5 shampoo |
|---|---|---|---|---|---|
| Invention 1 + 3 | Dried hair | 5 | 5 | 5 | 4 |
| Invention 2 + 3 | Dried hair | 5 | 5 | 4 | 3 |
| Invention 1 + 4 | Dried hair | 5 | 5 | 5 | 5 |
| Invention 1 + 5 | Dried hair | 5 | 5 | 5 | 5 |

The invention claimed is:

1. A hair dyeing process comprising:
applying to hair (1) a composition comprising at least one pigment and a maleic anhydride ethylenic polymer and (2) an amine compound selected from the group consisting of polyamine compounds bearing primary amine groups, polyamine compounds bearing secondary amine groups, polyamine compounds bearing secondary amino alkoxysilane groups, amino alkoxysilanes, and mixtures thereof,
the ethylenic polymer being derived from the polymerization of:
(a) 45% to 95% by weight, relative to the total weight of monomers, of an ethylenic monomer bearing an at least $C_8$ linear or branched alkyl group;
(b) 5% to 25% by weight of maleic anhydride;
(c) 0 to 50% by weight of additional monomer selected from the group consisting of:
(i) polydimethylsiloxane silicone monomers bearing a mono(meth)acryloyloxy end group of formula (I) below:

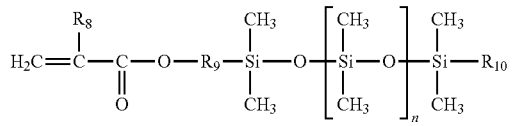

(I)

in which:
$R_8$ denotes a hydrogen atom or a methyl group;
$R_9$ denotes a linear or branched divalent hydrocarbon-based group containing from 1 to 10 carbon atoms and optionally containing one or two ether bonds —O—;
$R_{10}$ denotes a linear or branched alkyl group containing from 1 to 10 carbon atoms;
n denotes an integer ranging from 1 to 300; and
(ii) linear or branched $C_1$-$C_6$ alkyl (meth)acrylate or $C_6$-$C_{12}$ cycloalkyl (meth)acrylate non-silicone monomers;
the composition contains less than 2% of water when the amine compound is an amino alkoxysilane.

2. The hair dyeing process according to claim 1, comprising either (A) the sequential application to the hair of (1) the composition comprising a maleic anhydride ethylenic polymer and (2) the amine compound selected from the group consisting of polyamine compounds bearing primary amine groups, polyamine compounds beating secondary amine groups, polyamine compounds bearing secondary amino alkoxysilane groups, and mixtures thereof, or a composition containing the amine compound; or (B) the application to the hair of a composition derived from the mixing of ((1) the composition comprising a maleic anhydride ethylenic polymer and (2) the amine compound selected from the group consisting of amino alkoxysilanes, or a composition containing the amine compound.

3. The hair dyeing process according to claim 1, wherein the ethylenic monomer bearing an at least C8 linear or branched alkyl group is selected from the group consisting of:
a) linear or branched $C_8$-$C_{22}$ alkyl (meth)acrylates;
b) (meth)acrylamides of formula $CH_2$=$C(R_1)$—$CONR_3R_4$ in which $R_1$ represents a hydrogen atom or a methyl radical, $R_3$ represents a hydrogen atom or a linear or branched $C_1$-$C_{12}$ alkyl group, and $R_4$ represents a linear or branched $C_8$ to $C_{12}$ alkyl group;
c) vinyl esters of formula $R_5$—CO—O—CH=$CH_2$ in which $R_5$ represents a linear or branched $C_8$-$C_{22}$ alkyl group; and
d) ethers of formula $R_6$—O—CH=$CH_2$ in which $R_6$ represents a linear or branched $C_8$-$C_{22}$ alkyl group.

4. The hair dyeing process according to claim 1, wherein the ethylenic monomer bearing an at least $C_8$ linear or branched alkyl group is selected from the group consisting of $C_8$-$C_{22}$ alkyl (meth)acrylates.

5. The hair dyeing process according to claim 1, wherein the ethylenic monomer bearing an at least $C_8$ linear or branched alkyl group is selected from the group consisting of 2-ethylhexyl acrylate, 2-ethylhexyl methacrylate, lauryl acrylate, lauryl methacrylate, behenyl acrylate, behenyl methacrylate, stearyl acrylate, and stearyl methacrylate.

6. The hair dyeing process according to claim 1, wherein the ethylenic monomer bearing an at least $C_8$ linear or branched alkyl group is present in said ethylenic polymer in a content ranging from 45% to 90% by weight relative to the total weight of monomers.

7. The hair dyeing process according to claim 1, wherein maleic anhydride is present in said ethylenic polymer in a content ranging from 10% to 25% by weight relative to the total weight of monomers.

8. The hair dyeing process according to claim 1, wherein an additional monomer is present in the ethylenic polymer, and the additional monomer is a silicone monomer of formula (I) in which:
$R_8$ denotes a methyl group;
$R_9$ denotes a linear divalent hydrocarbon-based group containing from 2 to 4 carbon atoms;
$R_{10}$ denotes a linear or branched alkyl group, comprising from 2 to 8 carbon atoms;
n denotes an integer ranging from 3 to 200.

9. The hair dyeing process according to claim 1, wherein an additional monomer is present in the ethylenic polymer, and the additional monomer is non-silicone and is selected from the group consisting of $C_6$-$C_{12}$ cycloalkyl (meth) acrylates.

10. The hair dyeing process according to claim 1, wherein said ethylenic polymer comprises said additional silicone monomer of formula (I).

11. The hair dyeing process according to claim 1, wherein said ethylenic polymer comprises an additional monomer present in a content ranging from 5% to 50% by weight, relative to the total weight of monomers.

12. The hair dyeing process according to claim 1, wherein said ethylenic polymer does not contain any additional monomer.

13. The hair dyeing process according to claim 1, wherein said ethylenic polymer comprises:
(a) 75% to 95% by weight, relative to the total weight of monomers, of linear or branched $C_8$-$C_{22}$ alkyl (meth) acrylate;
(b) 5% to 25% by weight of maleic anhydride.

14. The hair dyeing process according to claim 1, wherein said ethylenic polymer is selected from the group consisting of the following copolymers:
  2-ethylhexyl acrylate/maleic anhydride,
  stearyl acrylate/maleic anhydride, and
  2-ethylhexyl acrylate/stearyl acrylate/maleic anhydride.

15. The hair dyeing process according to claim 1, wherein said ethylenic polymer comprises:
  (a) 45% to 94.5% by weight, relative to the total weight of monomers, of linear or branched $C_8$-$C_{22}$ alkyl (meth) acrylate;
  (b) 5% to 25% by weight of maleic anhydride;
  (c) 0.5% to 50% by weight of silicone monomer (I).

16. The hair dyeing process according to claim 1, wherein said ethylenic polymer is selected from the group consisting of the following copolymers:
  2-ethylhexyl acrylate/maleic anhydride/silicone monomer (I),
  stearyl acrylate/maleic anhydride/silicone monomer (I), and
  2-ethylhexyl acrylate/stearyl acrylate/maleic anhydride/silicone monomer (I).

17. The hair dyeing process according to claim 1, wherein said ethylenic polymer comprises:
  (a) 45% to 94.5% by weight, relative to the total weight of monomers, of linear or branched $C_8$-$C_{18}$ alkyl (meth) acrylate;
  (b) 5% to 25% by weight of maleic anhydride;
  (c) 0.5% to 50% by weight of $C_6$-$C_{12}$ cycloalkyl (meth) acrylate.

18. The hair dyeing process according to claim 1, wherein said ethylenic polymer is selected from the group consisting of the following copolymers:
  2-ethylhexyl acrylate/maleic anhydride/isobornyl (meth) acrylate,
  stearyl acrylate/maleic anhydride/isobornyl (meth)acrylate, and
  2-ethylhexyl acrylate/stearyl acrylate/maleic anhydride/isobornyl (meth)acrylate.

19. The hair dyeing process according to claim 1, wherein said ethylenic polymer comprises:
  (a) 45% to 94.5% by weight, relative to the total weight of monomers, of linear or branched $C_8$-$C_{18}$ alkyl (meth) acrylate;
  (b) 5% to 25% by weight of maleic anhydride;
  (c) 0.5% to 50% by weight of a mixture of $C_6$-$C_{12}$ cycloalkyl (meth)acrylate and of silicone monomer (I).

20. The hair dyeing process according to claim 1, wherein said ethylenic polymer is selected from the group consisting of the following copolymers:
  2-ethylhexyl acrylate/maleic anhydride/isobornyl (meth) acrylate/silicone monomer (I),
  stearyl acrylate/maleic anhydride/isobornyl (meth)acrylate/silicone monomer (I), and
  2-ethylhexyl acrylate/stearyl acrylate/maleic anhydride/isobornyl (meth)acrylate/silicone monomer (I).

21. The hair dyeing process according to claim 1, wherein the ethylenic polymer has a weight-average molecular weight ranging from 5000 to 1 000 000 g/mol.

22. The hair dyeing process according to claim 1, wherein, the ethylenic polymer is present in the composition in a content ranging from 0.1% to 40% by weight, relative to the total weight of the composition.

23. The hair dyeing process according to claim 1, wherein the amine compound comprises from 2 to 20 carbon atoms.

24. The hair dyeing process according to claim 1, wherein the amine compound is selected from the group consisting of N-methyl-1,3-diaminopropane, N-propyl-1,3-diaminopropane, N-isopropyl-1,3-diaminopropane, N-cyclohexyl-1,3-diaminopropane, 2-(3-aminopropylamino)ethanol, 3-(2-aminoethyl)aminopropylamine, bis(3-aminopropyl)amine, methylbis(3-aminopropyl)amine, N-(3-aminopropyl)-1,4-diaminobutane, N,N-dimethyldipropylenetriamine, 1,2-bis(3-aminopropylamino)ethane, N,N'-bis(3-aminopropyl)-1,3-propanediamine, ethylenediamine, 1,3-propylenediamine, 1,4-butylenediamine, lysine, cystamine, xylenediamine, tris(2-aminoethyl)amine and spermidine.

25. The hair dyeing process according to claim 1, wherein the amine compound has a weight-average molecular weight ranging from 500 to 1 000 000.

26. The hair dyeing process according to claim 25, wherein the amine compound is selected from the group consisting of poly(($C_2$-$C_5$)alkyleneimines); poly(allylamine); polyvinyl amines and copolymers thereof; vinylamine/vinylformamide copolymers; polyamino acids bearing $NH_2$ groups; aminodextran; amino polyvinyl alcohol, acrylamidopropylamine-based copolymers; chitosans;
  polydimethylsiloxanes comprising primary amine groups at the chain end or on side chains of formula (A) or (B) or (C):

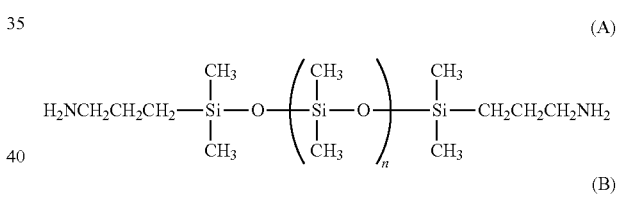

(A)

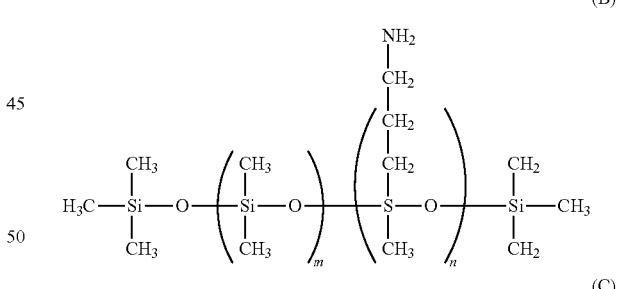

(B)

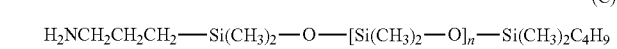

(C)

wherein
  in formula (A): the value of n is such that the weight-average molecular weight of the silicone is between 500 and 55 000;
  in formula (B), the values of n and m are such that the weight-average molecular weight of the silicone is between 1000 and 55 000;
  in formula (C), the value of n is such that the weight-average molecular weight of the silicone is between 500 and 3000;

amodimethicones of formula (D):

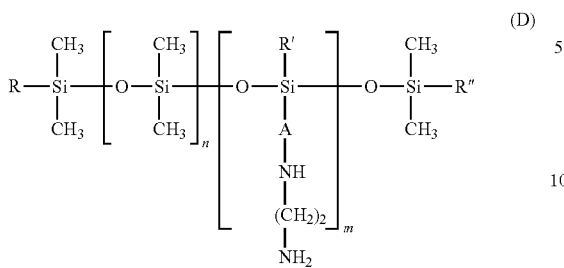

in which R, R' and R", which may be identical or different, each represent a $C_1$-$C_4$ alkyl or hydroxyl group, A represents a $C_3$ alkylene group and m and n are such that the weight-average molecular mass of the compound is between 5000 and 500 000;
polyetherdiamines;
polyamidoamine dendrimers bearing amine end functions;
poly(meth)acrylates bearing primary or secondary amine side functions; and poly(meth)acrylamides bearing primary or secondary amine side functions.

27. The hair dyeing process according to claim 1, wherein the amine compound is an amino alkoxysilane of formula (III):

$$R'_1Si(OR'_2)_z(R'_3) \quad (III)$$

in which:
R'$_1$ is a linear or branched, saturated or unsaturated, cyclic or acyclic $C_1$-$C_6$ hydrocarbon-based chain substituted with a group selected from the group consisting of the following groups:
amine $NH_2$ or NHR with R=$C_1$-$C_4$ alkyl,
an aryl or aryloxy group substituted with an amino group or with a $C_1$-$C_4$ aminoalkyl group,
R'$_1$ optionally containing a heteroatom or a carbonyl group, R'$_1$ being linked to the silicon atom directly via a carbon atom,
R'$_2$ and R'$_3$, which may be identical or different, represent a linear or branched alkyl group comprising from 1 to 6 carbon atoms,
z denotes an integer ranging from 1 to 3, and
x denotes an integer ranging from 0 to 2,
with z+x=3.

28. The hair dyeing process according to claim 1, wherein the amine compound is applied in a mole ratio of amine group of the amine compound/maleic anhydride group of the ethylenic polymer ranging from 0.01 to 10.

29. The hair dyeing process according to claim 1, wherein the composition(s) used comprise at least one pigment in an amount of between 0.5% and 40% by weight relative to the weight of the composition containing them or of the composition applied to the hair.

30. The hair dyeing process according to claim 1, wherein the composition comprising the maleic anhydride ethylenic polymer is applied first to the hair, and the amine compound or a composition containing the amine compound is then applied.

31. The hair dyeing process according to claim 1, wherein the amine compound, or a composition containing the amine compound, is applied first to the hair, and the composition comprising the maleic anhydride ethylenic polymer is then applied.

32. The hair dyeing process according to claim 1, wherein a composition derived from the mixing of (1) the composition comprising a maleic anhydride acrylic polymer and (2) the amine compound or a composition containing the amine compound, is applied topically to the hair.

33. The hair dyeing process according to claim 1 wherein the composition comprising the ethylenic polymer also comprises a non volatile oil.

\* \* \* \* \*